US008625862B2

(12) United States Patent
Sakaguchi

(10) Patent No.: US 8,625,862 B2
(45) Date of Patent: Jan. 7, 2014

(54) IMAGE DISPLAY METHOD AND IMAGE DISPLAY APPARATUS

(75) Inventor: Takuya Sakaguchi, Shioya-gun (JP)

(73) Assignees: Kabushiki Kaisha Toshiba, Tokyo (JP); Toshiba Medical Systems Corporation, Otawara-shi (JP)

( * ) Notice: Subject to any disclaimer, the term of this patent is extended or adjusted under 35 U.S.C. 154(b) by 1038 days.

(21) Appl. No.: 11/938,468

(22) Filed: Nov. 12, 2007

(65) Prior Publication Data

US 2008/0118126 A1 May 22, 2008

(30) Foreign Application Priority Data

Nov. 17, 2006 (JP) .................................. 2006-311775

(51) Int. Cl.
*A61B 6/00* (2006.01)
(52) U.S. Cl.
USPC .............................. 382/128; 382/131; 378/4
(58) Field of Classification Search
USPC ....................................................... 382/128
See application file for complete search history.

(56) References Cited

U.S. PATENT DOCUMENTS

| 4,855,910 | A  | * | 8/1989  | Bohning       | 324/309 |
|-----------|----|---|---------|---------------|---------|
| 7,505,550 | B2 | * | 3/2009  | Goto et al.   | 378/4   |
| 2002/0172409 | A1 | * | 11/2002 | Saito et al.  | 382/132 |
| 2006/0251300 | A1 | * | 11/2006 | Borgert et al.| 382/128 |

FOREIGN PATENT DOCUMENTS

| JP | 62-72329 | 4/1987 |
| JP | 2-196383 | 8/1990 |
| JP | 10-165387 | 6/1998 |
| JP | 2006-68350 | 3/2006 |
| WO | WO 2006/033377 | 3/2006 |

OTHER PUBLICATIONS

Japanese Office Action issued Mar. 5, 2013, in Japan Patent Application No. 2006-311775 (with English translation).
Japanese Office Action with English translation issued Mar. 13, 2012, in Japanese Patent Application No. 2006-311775, filed Nov. 17, 2006.

* cited by examiner

*Primary Examiner* — Phillip A Johnston
(74) *Attorney, Agent, or Firm* — Oblon, Spivak, McClelland, Maier & Neustadt, L.L.P.

(57) ABSTRACT

An image data apparatus comprises a view angle defining section for defining a plurality of view angles relative to an object of examination, an image data preparing section for preparing a plurality of three-dimensional image data for the plurality of view angles from four-dimensional image data of the object of examination and a display control section for displaying moving images of the three-dimensional image data of the object of examination on a monitor screen under the condition that the view angles are fixed.

12 Claims, 21 Drawing Sheets

| W₁ ![curve] F₁=RAO30, CRA20 | W₂ ![curve] F₂=0, CRA20 | W₃ ![curve] F₃=LAO50, CRA20 |
|---|---|---|
| W₄ ![curve] F₄=RAO30, 0 | W₅ ![curve] P F₅=0, 0 | W₆ ![curve] F₆=LAO50, 0 |
| W₇ ![curve] F₇=RAO30, CAU30 | W₈ ![curve] F₈=0, CAU30 | W₉ ![curve] F₉=LAO50, CAU30 |

~20a

IMAGE DISPLAY METHOD AND IMAGE DISPLAY APPARATUS

CROSS-REFERENCE TO RELATED APPLICATIONS

This application is based upon and claims the benefit of priority from prior Japanese Patent Application No. 2006-311775, filed Nov. 17, 2006, the entire contents of which are incorporated herein by reference.

BACKGROUND OF THE INVENTION

1. Field of the Invention

This invention relates to an image display method and an image display apparatus for displaying a moving image of an object of examination such as a coronary artery for determining an optimum direction of observation of the object by a medical X-ray apparatus when reading the moving image of the object that can be acquired by means of a medical equipment such as an X-ray diagnostic apparatus for intravascular surgery (intervention).

2. Description of the Related Art

Objects of examination of human bodies include coronary arteries. Coronary arteries surround the heart as blood vessels to supply blood to the muscles of the heart. A serious condition arises when any of the coronary arteries falls into a morbid state such as stenosis. An intravascular intervention using an X-ray diagnostic apparatus is brought in to cure such a disease.

An intravascular intervention using an X-ray diagnostic apparatus is a risky manual operation of driving a surgery device into a coronary artery. For the intervention, the detector of the X-ray diagnostic apparatus is rigidly secured in position and X-rays are continuously irradiated from a selected view angle, while the operator proceeds with the manipulation, seeing the image of the blood vessel being displayed on the monitor screen as object of examination. The manipulation can be facilitated when the operator can see an image of the blood vessel taken from an optimal view angle.

FIGS. 28 and 29 of the accompanying drawings show how a part of a human body appears in tow different view angles. The view angles include view angle θ illustrated in FIG. 28 and view angle ø illustrated in FIG. 29. By turn, the view angle θ is expressed in terms of a head direction (CRA) and a tail direction (CAU) relative to the object of examination 1 of a human body, whereas the view angle ø is expressed in terms of a first tilt direction (RAO) and a second tilt direction (LAO) relative to the object of examination 1.

However, when the view angle is shifted from an optimal view angle during the intervention, the coronary artery in question may be overlapped with other blood vessel or a branching blood vessel may be overlapped with the coronary artery to consequently give rise to a phenomenon of foreshortening, where the coronary artery appears shorter than its proper length. Such a phenomenon makes the manipulation of the intervention difficult. Therefore, it is important to find out an optimal view angle from the information acquired before the intervention. In the case of a coronary artery, foreshortening is a phenomenon that makes the length of the coronary artery projected onto a two-dimensional plane appear shorter than the length of the coronary artery actually running in a three-dimensional space. Foreshortening 0% refers to that the actual length of the coronary artery is equal to the apparent length thereof and foreshortening 100% refers to that the coronary artery appears simply as a spot.

There is a technique of determining an optimal view angle for an intervention. With this technique, a technology of three-dimensionally displaying a rotating coronary artery (coronary 3D, coronary tree) on a monitor screen on the basis of X-ray images in two directions is employed to determine an optimal view angle. This technique has become popular for clinical applications.

FIG. 30 of the accompanying drawings schematically illustrates how a three-dimensional image is structured by epipolar geometry. For example, let us refer to the projected image of coronary artery 1a of a human body picked up by imaging the coronary artery from a frontal direction as Frontal Image 2 and the projected image picked up by imaging the coronary artery from a direction different from the frontal direction, or a lateral direction, as Lateral Image 3. The part of the coronary artery 1a projected on point A on the Lateral Image 3 is found somewhere on line B but cannot be identified. The line B is projected onto line C on the Frontal Image 2. The coronary artery 1a is projected somewhere on the line C. Thus, as the operator of the intervention manually specifies the corresponding point on the Frontal Image 2, the position of the coronary artery 1a in a three-dimensional space is defined. In other words, it is necessary to specify the coordinates of the point on the Frontal Image 2 and those of the corresponding point on the Lateral Image 3 in order to identify the three-dimensional position of the coronary artery 1a.

FIG. 31 schematically illustrates how a rotating blood vessel is displayed three-dimensionally on a monitor screen. The rotating blood vessel is displayed three-dimensionally as a moving image that is obtained when the coronary artery 1a is observed in the first tilt direction (RAO) and the second tilt direction (LAO) and the view angle (point of view) is shifted. Each of the arrows in the three-dimensional images of the blood vessel indicates the rotating/moving direction of the coronary artery 1a.

More specifically, a moving image that is obtained when the view angle is continuously shifted with time to RAO=50°, RAO=90°, RAO=130°, . . . , LAO=10° is displayed on a monitor screen. Only the view angles of RAO and LAO of RAO=50°, RAO=90°, RAO=130°, . . . , LAO=10° are shown for the purpose of simplicity. The moving image that is obtained as the view angle is shifted relative to the coronary artery 1a appears as a rotating image of the coronary artery 1a. Thus, an optimal view angle can be determined from the rotating image of the coronary artery 1a being displayed on the monitor screen.

An optimal view angle is such that, for example, (a) an angle that makes the morbid part, e.g., a stenotic part, appear longest, which is an angle that makes branched blood vessels, if any, appear wide open, (b) an angle that makes the morbid part, e.g., a stenotic part, appear narrowest, (c) an angle that makes the morbid part, e.g., a stenotic part, free from any other overlapping blood vessel or (d) an angle that makes the morbid part appear moving least.

Blood vessels change their positions as the heart beats. An optimal view angle is determined for a blood vessel so as to structure a three-dimensional blood vessel image in a cardiac phase at a moment of the moving blood vessel and satisfy above (a), (b), (c). However, the determined optimal view angle cannot necessarily be optimal in all the cardiac phases. In other words, if such a view angle is optimal in a cardiac phase, it may not necessarily be so in other cardiac phases and hence the requirements of above (a), (b), (c) may not necessarily be satisfied in other cardiac phases. Additionally, it is not possible to determine an optimal view angle in terms of (d) an angle that makes the morbid part appear moving least. For example, if any other blood vessel does not overlap the coronary artery 1a in a cardiac phase, the coronary artery 1a is more often than not hidden by some other blood vessel to make an intervention difficult.

A heat phase can be explained by means of an electrocardiogram signal as follows. An electrocardiogram (ECG) is obtained by sensing the movement of the heart as an electrical signal. As shown in FIG. 32 of the accompanying drawings, an R-wave appears when the ventricle begins contraction. A cardiac phase shows a temporal phase of the electrocardiogram signal E in the time interval from an R-wave to the next R-wave. Generally, an R-wave is defined as 0% temporal phase and the next R-wave is defined as 100% temporal phase and the temporal phase at any moment in the time interval is determined by means of the temporal ratio of the moment. For example, an end-diastolic phase is expressed to be at or near 75% temporal phase.

As pointed out above, the determined optimal view angle cannot necessarily be optimal in all the cardiac phases. To solve this problem, a technique of preparing four-dimensional data of (x, y, z, t) including three-dimensional spatial image data of (x, y, z) and temporal elements (t) and determining an optimal view angle for all the cardiac phases by means of these four-dimensional data may be conceivable.

However, the data obtained by means of such a technique include both information acquired when the view angle is shifted and information on the movement of the heart. Then, the image displayed on the monitor screen is a three-dimensional image of a blood vessel that is obtained when the view angle is shifted to which the heartbeat movement is added. When both the shift of the view angle and the heartbeat movement are displayed on the monitor screen, the movement of the coronary artery 1a shown on the monitor screen becomes complicated to make it difficult to determine an optimal view angle. Determine separately an optimal view angle by shifting the view angle and also an optimal view angle in a cardiac phase results in determining only a locally optimal view angle to make it very time consuming to determine an optimal view angle for all the cardiac phases. Known documents relating to this technical field include U.S. Pat. No. 6,501,848.

The present invention provides an image display method and an image display apparatus that can display an image for determining an optimal view angle in a short period of time.

BRIEF SUMMARY OF THE INVENTION

In the first aspect of the present invention, there is provided an image display method comprising: defining a plurality of display mode conditions for displaying an image of an object of examination showing a periodic contracting movement on a monitor screen; preparing a plurality of three-dimensional image data including temporal elements and corresponding to the plurality of display mode conditions from four-dimensional data including temporal elements of the object of examination; fixing the plurality of display mode conditions and displaying a three-dimensional image in each of the display mode conditions, switching the three-dimensional image data.

In the second aspect of the present invention, there is provided an image display apparatus comprising: a view angle defining section which defines a plurality of view angles relative to an object of examination showing a periodic contracting movement; a monitor having a monitor screen; an image data preparing section which prepares a plurality of three-dimensional image data including temporal elements in a plurality of view angles from four-dimensional image data on the object of examination including temporal elements; and a display control section which displays a moving image of the plurality of three-dimensional image data of the object of examination showing a contracting movement on the monitor screen under the condition of fixing the plurality of view angles.

In the third aspect of the present invention, there is provided an image display apparatus comprising: a phase defining section which defines a plurality of phases of a contracting movement of an object of examination showing a periodic contracting movement; a monitor having a monitor screen; an image data preparing section which prepares a plurality of three-dimensional image data including temporal elements of shifting the view angle relative to the object of examination for each of a plurality of phases from four-dimensional image data on the object of examination including temporal elements; and a display control section which displays a moving image of each of the plurality of three-dimensional image data of the object of examination showing a contracting movement on the monitor screen under the condition of fixing the phases, shifting the view angle.

In the fourth aspect of the present invention, there is provided an image display apparatus comprising: an image data preparing section which prepares a plurality of three-dimensional image data including temporal elements on an object of examination showing a periodic movement; a color information defining section which defines a plurality of pieces of color information corresponding to the quantity of contracting movement of the object of examination; a monitor having a monitor screen; and a display control section which displays an image on the monitor screen, adding the color information to the plurality of three-dimensional image data.

In the fifth aspect of the present invention, there is provided an image display apparatus comprising: an image data preparing section which prepares a first three-dimensional image data of an arbitrarily selected view angle including temporal elements from four-dimensional image data including temporal elements on an object of examination showing a periodic contracting movement and a second three-dimensional image data of a view angle shifted from the above view angle relative to the object of examination under the condition of fixing the contracting movement of the object of examination from the four-dimensional image data; a monitor having a monitor screen; and a display control section which displays the image of the first three-dimensional image data and the image of the second three-dimensional image data prepared by the image data preparing section in a switched manner.

Additional objects and advantages of the invention will be set forth in the description which follows, and in part will be obvious from the description, or may be learned by practice of the invention. The objects and advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate embodiments of the invention, and together with the general description given above and the detailed description of the embodiments given below, serve to explain the principles of the invention.

DETAILED DESCRIPTION OF THE INVENTION

Now, the first embodiment of the present invention will be described by referring to the related ones of the accompanying drawings.

Figure 1:
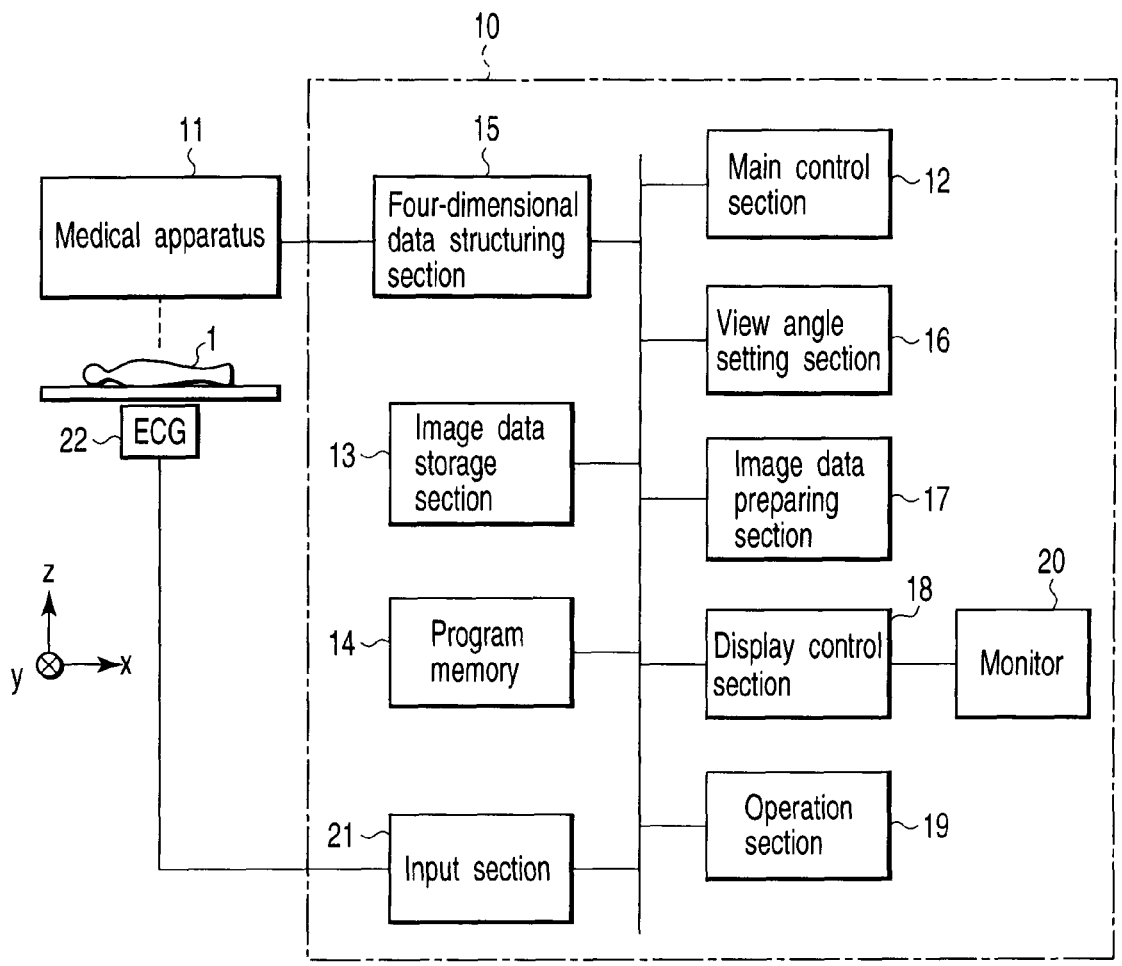
FIG. 1 is a schematic block diagram of a first embodiment of image display apparatus according to the present invention.

FIG. 1 is a schematic block diagram of the first embodiment of image display apparatus according to the present invention. Referring to FIG. 1, medical equipment 11 is connected to the main body 10 of the image display apparatus. The medical equipment 11 images an object of examination 1 that shows a periodic contracting movement such as the coronary arteries 1a extending around and surrounding a heart showing a heartbeat movement and acquires image data on the object. The medical equipment 11 may typically be an X-ray apparatus, an X-ray computed tomography (X-ray CT) apparatus, a magnetic resonance imaging (MRI) apparatus, a positron emission computed tomography (PET) apparatus, a single-photon-emission computed tomography (SPECT) apparatus, an ultrasound diagnosis (US) apparatus, intravascular ultrasound (IVUS), or an X-ray diagnostic apparatus.

The image display apparatus main body 10 processes the image data and displays an image of a coronary artery 1a. The image display apparatus main body 10 has a main control section 12 that includes a CPU. The main control section 12 is connected to an image data storage section 13 and a program memory 14. The main control section 12 issues commands to operate a four-dimensional data structuring section 15, a view angle setting section 16, an image data preparing section 17, a display control section 18 and an operation section 19 that typically includes a keyboard, a mouse and ten keys. A monitor 20 such as a liquid crystal display is connected to the display control section 18. An input section 21 is connected to the main control section 12. An electrocardiograph (ECG) 22 is connected to the input section 21. The electrocardiograph 22 outputs the movement of the object of examination 1, or the heart, as electrocardiogram signal E. For example, the surgeon who is going to perform an intravascular intervention operates the operation section 19 when he or she needs to determine an optimal view angle relative to the coronary artery 1a of the object of examination 1.

Figure 2:
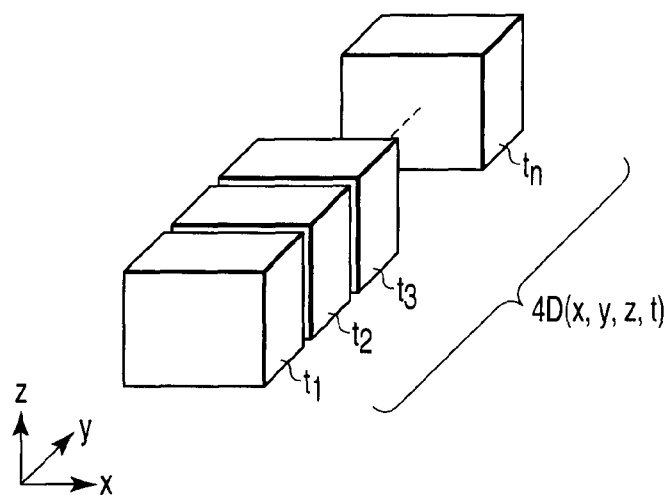
FIG. 2 is a schematic illustration of four-dimensional image data structured by the four-dimensional data structuring section of the apparatus of the first embodiment.

The four-dimensional data structuring section 15 receives the image data on the object of examination 1 acquired by the medical equipment 11 and structures four-dimensional image data (x, y, z, t) as shown in FIG. 2 from the image data. Such four-dimensional image data 4D are prepared by volume rendering, which is a technique for three-dimensional display. Such four-dimensional image data 4D are prepared by maximum intensity projection (MIP). Maximum intensity projection (MIP) is being popularly used for displaying blood vessels by means of an MRI apparatus, an X-ray CT apparatus or a US apparatus. Four-dimensional image data 4D are formed by image data of a three-dimensional space (x, y, z) and temporal elements (t). The four-dimensional image data 4D are then stored in the image data storage section 13.

Figure 28:
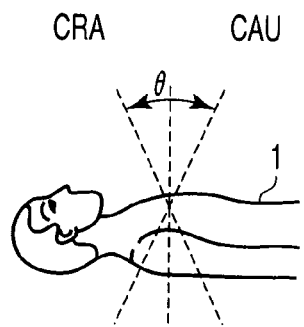
FIG. 28 is a schematic illustration of a view angle in terms of CRA and CAU.
Figure 29:
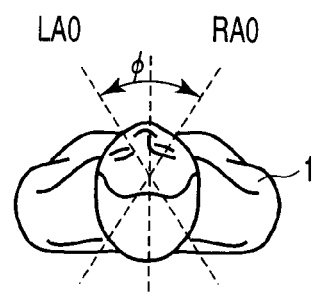
FIG. 29 is a schematic illustration of a view angle in terms of RAO and LAO.

The view angle setting section 16 typically selects a plurality of view angles relative to the coronary artery 1a of the object of examination 1. Each of the view angles is set by an input operation of the surgeon who is going to perform an intravascular intervention. Each view angle is defined by view angle θ that is expressed in terms of a head direction (CRA) and a tail direction (CAU) relative to the object of examination 1 as shown in FIG. 28 and view angle ø that is expressed in terms of a first tilt direction (RAO) and a second tilt direction (LAO) relative to the object of examination 1 as shown in FIG. 29.

The plurality of view angles $F_1, F_2, F_3, \ldots, F_j$ are set, for example, as nine (j=9) fixed view angles including $F_1$ (RAO 30°, CRA 20°), $F_2$ (0°, CRA 20°), $F_3$ (LAO 50°, CRA 20°), $F_4$ (RAO 30°, 0°), $F_5$ (0°, 0°), $F_6$ (LAO 50°, 0°), $F_7$ (RAO 30°, CAU 30), $F_8$ (0°, CAU 30°) and $F_9$ (LAO 50°, CAU 30°). Note, however, that view angles are not limited to the above nine view angles of $F_1, F_2, F_3, \ldots, F_9$ and can be arbitrarily selected by the surgeon who is going to perform an intravascular intervention. For the purpose of the present invention, view angle, view point and view direction are synonyms.

Figures 3, 4:
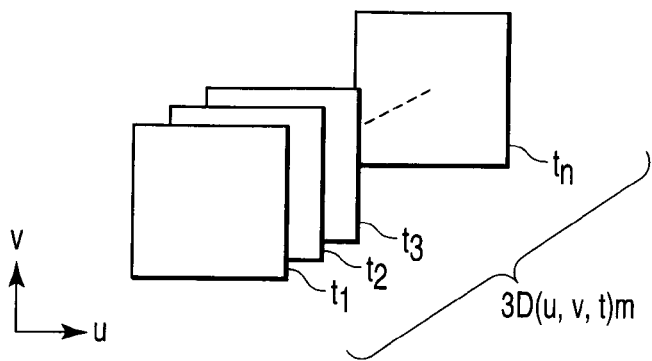
FIG. 3 is a schematic illustration of a plurality of three-dimensional image data prepared by the image data preparing section of the apparatus of the first embodiment.
FIG. 4 is a schematic illustration of a plurality of three-dimensional image data displayed as synopsis on the monitor screen by the display control section of the apparatus of the first embodiment.

The image data preparing section 17 prepares a plurality of three-dimensional image data (u, v, t) 3D including temporal elements t for the plurality of view angles as shown in FIG. 3 from the four-dimensional image data 4D. Three-dimensional image data 3D include image data of a two-dimensional space (u, v) and temporal elements t. As a plurality of view angles $F_1, F_2, F_3, \ldots, F_j$ are selected and set by the view angle setting section 16, the image data preparing section 17 prepares three-dimensional image data $3D_1, 3D_2, 3D_3, \ldots, 3D_j$ respectively for the plurality of view angles $F_1, F_2, F_3, \ldots, F_j$. The three-dimensional image data $3D_1, 3D_2, 3D_3, \ldots, 3D_j$ are used to produce so many moving images of the coronary artery 1a that moves in response to the heartbeat under the condition that the view angles $F_1, F_2, F_3, \ldots, F_j$ are fixed and set.

The display control section 18 displays the moving images of the three-dimensional image data $3D_1, 3D_2, 3D_3, \ldots, 3D_j$ of the coronary artery 1a extending around and surrounding the beating heart that shows a heartbeat movement on the monitor screen 20a of the monitor 20 under the condition that the view angles $F_1, F_2, F_3, \ldots, F_j$ are fixed. More specifically, the display control section 18 defines a plurality of windows $W_1, W_2, W_3, \ldots, W_j$ on the monitor screen 20a and synoptically displays the three-dimensional images of the three-dimensional image data $3D_1, 3D_2, 3D_3, \ldots, 3D_j$ respectively in the windows $W_1, W_2, W_3, \ldots, W_j$, synchronizing the time elements t of the three-dimensional image data, as shown in FIG. 4.

As an example, the display control section 18 displays the related ones of RAO, LAO, CAU and CRA of each of the view angles $F_1, F_2, F_3, \ldots, F_j$ respectively at the left side, at the right side and at the lower side and at the upper side of each of the windows of the monitor screen 20a.

FIG. 4 shows nine windows $W_1$ through $W_9$ formed on the monitor screen 20a. However, the number of view angles $F_1$ through $F_j$ that is selected and set is not limited to nine and depends on the view angles that are frequently selected for intravascular interventions in the hospital, which may typically be about ten. Thus, the nine windows $W_1$ through $W_9$ are assigned respectively to the selected view angles $F_1, F_2, F_3, \ldots, F_j$. Therefore, moving images of the coronary artery 1a that moves in response to the heartbeat are displayed in the windows $W_1$ through $W_9$ under the condition that the corresponding view angles $F_1, F_2, F_3, \ldots, F_j$ are fixed and set.

Figure 32:
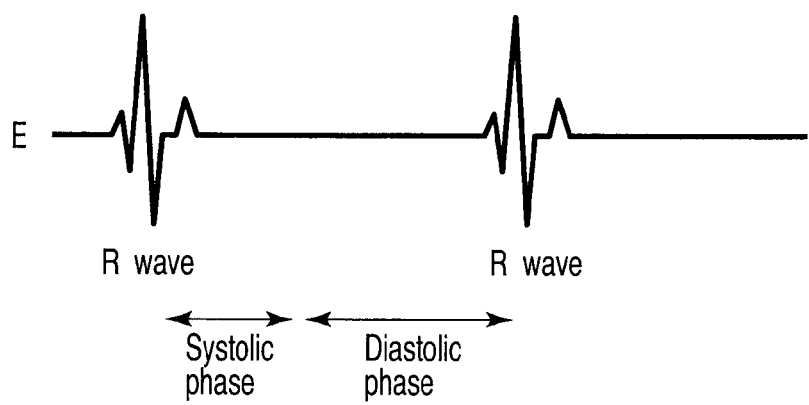
FIG. 32 is a schematic illustration of R-waves that appear when the ventricle of a heart contracts.

The display control section 18 receives as input the electrocardiogram signal E of the object of examination 1 output from the electrocardiograph 22 as shown in FIG. 32 and typically displays the electrocardiogram waveform at a corner of the monitor screen 20a.

The program memory 14 stores the image display program to be executed by the main control section 12. The image display program is adapted to cause the image display apparatus to select and set the view angles $F_1, F_2, F_3, \ldots, F_j$ relative to the coronary artery 1a that extends around and surrounds the heart showing a heartbeat movement, prepares a plurality of three-dimensional image data $3D_1, 3D_2, 3D_3, \ldots, 3D_j$ including temporal elements t for the view angles $F_1, F_2, F_3, \ldots, F_j$ from four-dimensional image data 4D of the coronary artery 1a including temporal elements t and displays the moving images of the three-dimensional image data $3D_1, 3D_2, 3D_3, \ldots, 3D_j$ of the coronary artery 1a on the monitor screen 20a.

Now, the image display operation of the image display apparatus having the above-described configuration will be described below.

The medical equipment 11 may typically be an X-ray apparatus, an X-ray CT apparatus, an MRI apparatus, a PET apparatus, a SPECT apparatus, a US apparatus, an IVUS apparatus or an X-ray diagnostic apparatus and adapted to image a coronary artery 1a that extends around and surrounds a heart showing a heartbeat movement and acquire data on the coronary artery 1a.

The four-dimensional data structuring section 15 receives the image data of the object of examination 1 acquired by the medical equipment 11 and structures four-dimensional image data 4D (x, y, z, t) as shown in FIG. 2 from the received image data. The structured four-dimensional image data 4D are stored in the image data storage section 13.

On the other hand, the view angle setting section 16 receives the input given to the operation section 19 by the surgeon who is going to perform an intravascular intervention and selects and sets the view angles $F_1$ through $F_j$ relative to the coronary artery 1a of the object of examination 1. Note that the suffix j indicates each view angle. The number of view angles $F_1$ through $F_j$ that is selected and set depends on the view angles that are frequently selected for intravascular interventions in the hospital, which may typically be about ten. The plurality of view angles $F_1, F_2, F_3, \ldots, F_j$ may be set as, for example, nine (j=9) fixed view angles including $F_1$ (RAO 30°, CRA 20°), $F_2$ (0°, CRA 20°), $F_3$ (LAO 50°, CRA 20°), $F_4$ (RAO 30°, 0°), $F_5$ (0°, 0°), $F_6$ (LAO 50°, 0°), $F_7$ (RAO 30°, CAU 30°), $F_8$ (0°, CAU 30°) and $F_9$ (LAO 50°, CAU 30°).

Then, the image data preparing section 17 reads the four-dimensional image data 4D from the image data storage section 13 and, at the same time, receives the nine (j=9) view angles $F_1, F_2, F_3, \ldots, F_9$ that are fixed and set by the view angle setting section 16. Then, the image data preparing section 17 prepares three-dimensional image data (u, v, t) 3D ($3D_1, 3D_2, 3D_3, \ldots, 3D_9$) as shown in FIG. 3 for the view angles $F_1, F_2, F_3, \ldots, F_9$ from the four-dimensional image data 4D. The three-dimensional image data $3D_1, 3D_2, 3D_3, \ldots, 3D_9$ produce respective moving images of the coronary artery 1a that moves in response to the heartbeat under the condition that the view angles $F_1, F_2, F_3, \ldots, F_j$ are fixed.

Figure 5:
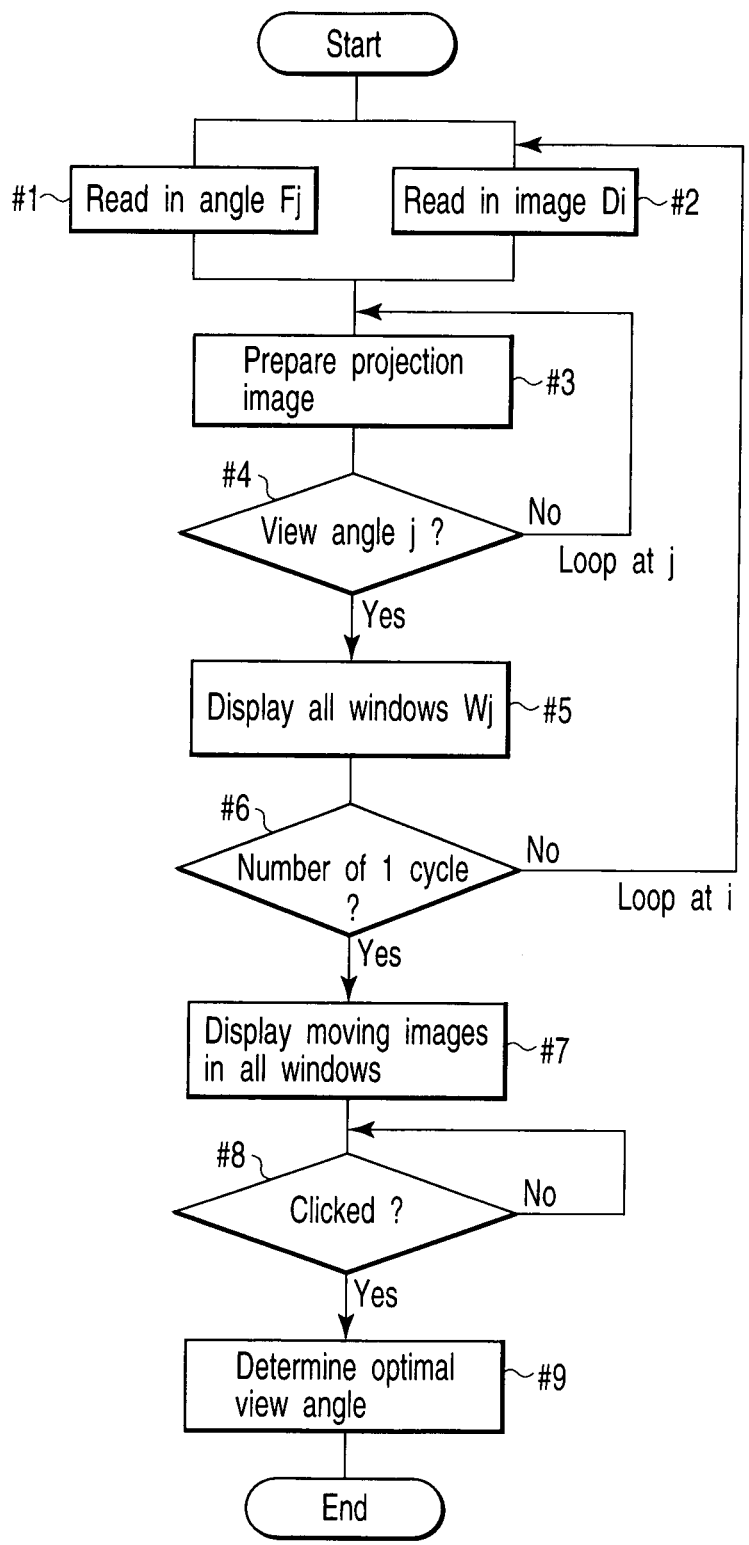
FIG. 5 is a flowchart of the process of preparing three-dimensional image data of three-dimensional images to be displayed in the respective windows of the monitor screen of the apparatus of the first embodiment.

Now, a specific method of preparing three-dimensional image data $3D_1, 3D_2, 3D_3, \ldots, 3D_9$ will be described below by referring to the three-dimensional image data preparing flowchart of FIG. 5. The process of the flowchart of FIG. 5 will be repeated for the nine moving images of the three-dimensional image data $3D_1, 3D_2, 3D_3, \ldots, 3D_9$ to be displayed in the respective windows $W_1$, through $W_9$.

Firstly, in Step #1, the image data preparing section 17 reads the nine (j=9) view angles $F_1, F_2, F_3, \ldots, F_9$ from the view angle setting section 16. Then, in Step #2, the image data preparing section 17 reads the four-dimensional image data 4D (x, y, z/t=$i_1$) of a cardiac phases $i_k$ (k=1, 2, 3, . . . , m) from the image data storage section 13.

Then, in Step #3, the image data preparing section 17 prepares projection image data (u, v/t=$i_1$) of a single image of the coronary artery 1a projected onto the view angle $F_1$ from the four-dimensional image data 4D (x, y, z/t=$i_1$) of the cardiac phase $i_1$ read for the view angle $F_1$. The projection image data (u, v/t=$i_1$) of the single image for the view angle $F_1$ are image data of a still image.

In Step #4, the image data preparing section 17 determines if projection image data (u, v/t=$i_1$) of a single image of the coronary artery 1a projected in each of all the view angles $F_1, F_2, F_3, \ldots, F_9$ are prepared or not. If projection image data (u, v/t=$i_1$) of a single image of the coronary artery 1a projected in each of all the view angles $F_1, F_2, F_3, \ldots, F_9$ are not prepared yet, the image data preparing section 17 returns to Step #3, where it prepares projection image data (u, v/t=$i_1$) of a single image of the coronary artery 1a projected onto the view angle $F_2$ from the four-dimensional image data 4D (x, y, z/t=$i_1$) of the cardiac phase $i_1$ read for the view angle $F_2$.

When it is determined that projection image data (u, v/t=$i_1$) of a single image of the coronary artery 1a projected in each of all the view angles $F_1, F_2, F_3, \ldots, F_9$ are prepared, the image data preparing section 17 proceeds to Step #5, where it sends the projection image data (u, v/t=$i_1$) for each of the view angles $F_1, F_2, F_3, \ldots, F_9$ to the display control section 18. The display control section 18 displays projection images of the projection image data (u, v/t=$i_1$) for all the view angles $F_1, F_2, F_3, \ldots, F_9$ in the respective windows on the monitor screen 20a as shown in FIG. 4. At this time, the projection images displayed in the respective windows $W_1$ through $W_9$ on the monitor screen 20a are still images.

Then, in Step #6, the image data preparing section 17 determines if the number of projection images for each of all the view angles $F_1, F_2, F_3, \ldots, F_9$ gets to the value necessary for forming a moving image or not. The number of projection images necessary for forming a moving image is the number necessary for continuously displaying a cycle of periodic contracting movement of the object of examination 1 as a moving image. If the object of examination 1 is a coronary artery 1a, the number of projection images necessary for forming a moving image is the number of projection image necessary for continuously displaying a single heartbeat as a moving image.

If, as a result of the determining step, it is determined that the number of projection images for each of all the view angles $F_1, F_2, F_3, \ldots, F_9$ does not get to the value necessary for forming a moving image, the image data preparing section 17 returns to Step #2. In Step #2, the image data preparing section 17 reads the four-dimensional image data 4D (x, y, z/t=$i_k$) of the next cardiac phase $i_k$, for example the four-dimensional image data 4D (x, y, z/k=$i_2$) of the cardiac phase $i_2$, from the image data storage section 13.

In this way, the image data preparing section 17 prepares projection image data (u, v/t=$i_2$) of a single projection image for each of all the view angles $F_1, F_2, F_3, \ldots, F_9$ in Steps #3 and #4. Then, in Step #5, the display control section 18 displays the projection images of the projection image data (u, v/t=$i_2$) in the respective windows $W_1$ through $W_9$ on the monitor screen 20a shown in FIG. 4 to immediately succeed the projection images of the projection image data (u, v, t=$i_1$) for all the view angles $F_1, F_2, F_3, \ldots, F_9$.

Thus, the image data preparing section 17 repeats Steps #1 through #6. As a result, the image data preparing section 17 gradually prepares projection image data (u, v/t=$i_1, 2, 3, \ldots, m$) for each of all the view angles $F_1, F_2, F_3, \ldots, F_9$.

When the number of projection images of the prepared projection image data gets to the value necessary for continuously displaying a heartbeat as a moving image, the image data preparing section 17 completes the operation of preparing three-dimensional moving images of the three-dimensional image data $3D_1, 3D_2, 3D_3, \ldots, 3D_9$ for each of the view angles $F_1, F_2, F_3, \ldots, F_9$. In other words, the three-dimensional image data $3D_1, 3D_2, 3D_3, \ldots, 3D_9$ are formed by image data of a two-dimensional space (u, v) and temporal elements t (=$i_1, 2, 3, \ldots, m$). The three-dimensional image data $3D_1, 3D_2, 3D_3, \ldots, 3D_9$ are those of moving images of the coronary artery 1a that move in response to a single heartbeat for the respective fixed view angles $F_1, F_2, F_3, \ldots, F_9$. Then, the image data preparing section 17 sends the three-dimensional image data $3D_1, 3D_2, 3D_3, \ldots, 3D_9$ to the display control section 18.

Figure 6:
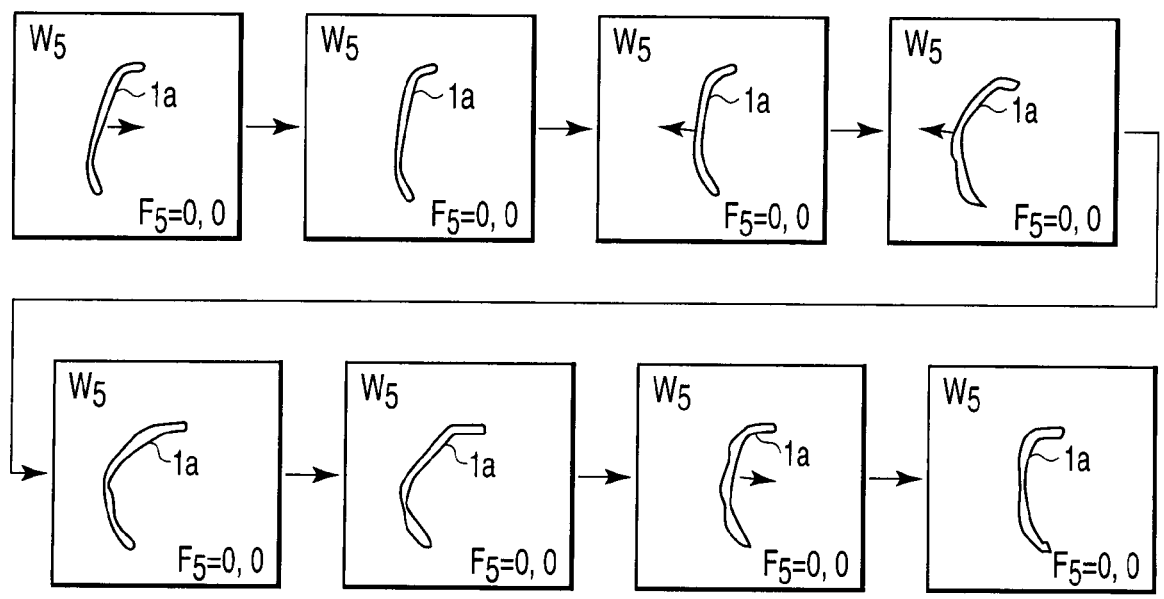
FIG. 6 is a schematic illustration of a moving image that can be displayed on the monitor screen of three-dimensional image data in a selected and fixed view angle.

In Step #7, the display control section 18 displays the moving images of the three-dimensional image data $3D_1, 3D_2, 3D_3, \ldots, 3D_9$ for all the view angles $F_1, F_2, F_3, \ldots, F_9$ in the respective windows $W_1$ through $W_9$ on the monitor screen 20a as shown in FIG. 4. As an example, FIG. 6 schematically illustrates the moving image of the three-dimensional image data $3D_5$ for the view angle $F_5$ that is displayed on the window $W_5$ on the monitor screen 20a. The moving image of the three-dimensional image data $3D_5$ is that of the coronary artery 1a moving in response to a single heartbeat under the condition that the view angle $F_5$ (0°, 0°) is fixed. The arrows in the windows showing the moving images indicate the moving direction of the coronary artery 1a that moves in response to the heartbeat.

While FIG. 6 shows the moving image of the three-dimensional image data $3D_5$ for the view angle $F_5$ that is displayed in the window $W_5$, the moving images of the three-dimensional image data $3D_1$ through $3D_4$ and $3D_6$ through $3D_9$ are displayed respectively in the remaining windows $W_1$ through $W_4$ and $W_6$ through $W_9$. The display control section 18 displays the moving images of the three-dimensional image data $3D_1, 3D_2, 3D_3, \ldots, 3D_9$ for the view angles $F_1, F_2, F_3, \ldots, F_9$ in the respective windows $W_1$ through $W_9$ in synchronism with the time elements t.

The display control section 18 displays the moving images of the three-dimensional image data $3D_1$ through $3D_9$ for the view angles $F_1, F_2, F_3, \ldots, F_9$ in the respective windows $W_1$ through $W_9$ at the replay speed that agrees with the moving speed of the heartbeat. However, the display control section 18 may set an arbitrarily selected speed that is input from the operation section 19 from the reply speed of the moving images of the three-dimensional image data $3D_1$ through $3D_9$. Alternatively, the display control section 18 may make the replay speed of the moving images agree with the rate at which it collects projection image data for preparing the three-dimensional image data $3D_1, 3D_2, 3D_3, \ldots, 3D_9$.

The display control section 18 receives the electrocardiogram signal E of the object of examination 1 output from the electrocardiograph 22 as shown in FIG. 32 and displays the waveform of the electrocardiogram at a corner of the monitor screen 20a, for instance. The replay speed of replaying the moving images of the three-dimensional image data $3D_1$ through $D_9$ that are displayed in the respective windows $W_1$ through $W_9$ agrees with the moving speed of the heartbeat. Thus, the surgeon can easily recognize the movement of the coronary artery 1a that corresponds to the heartbeat when the electrocardiogram is also displayed.

Then, in Step #8, the display control section 18 determines which one of the moving images of the three-dimensional image data $3D_1$ through $3D_9$ for the view angles $F_1$ through $F_9$ being displayed in the respective windows $W_1$ through $W_9$ is to be selected. The surgeon who performs an intravascular intervention operates the mouse, for instance, of the operation section 19 that works as view angle determining section. In response to the click operation of the mouse, pointer P may be placed on the window $W_5$ on the monitor screen 20a and clicked. Then, the display control section 18 recognizes the click. In Step #9, the display control section 18 determines the view angle $F_5$ (0°, 0°) of the window $W_5$ as optimal view angle for the intravascular intervention.

Then, the main control section 12 stores the view angle (0°, 0°) that is determined as optimal view angle in a memory such as RAM and also transmits it to the medical equipment 11. The main control section 12 has a transmission section that transmits information on the optimal view angle to the medical equipment 11 by way of the network, for instance.

The medical equipment 11 has an X-ray apparatus, for instance. The X-ray apparatus is equipped with a C arm for arranging an X-ray source and an X-ray detector opposite to each other. The X-ray apparatus includes a C arm drive section for driving the C arm to rotate and a C arm control section for controlling the drive operation of the C arm. The C arm control section receives the view angle $F_5$ (0°, 0°) that is determined as optimal view angle. The C arm control section sends out a drive control signal that corresponds to the view angle $F_5$ (0°, 0°) to the C arm drive section. The C arm drive section drives the C arm according to the drive control signal and moves the X-ray source and the source detector to respective positions that correspond to the view angle $F_5$ (0°, 0°). As a result, a moving image of the coronary artery 1a is obtained by imaging the coronary artery 1a in the view angle $F_5$ (0°, 0°) optimal for the intravascular intervention.

Figure 7:
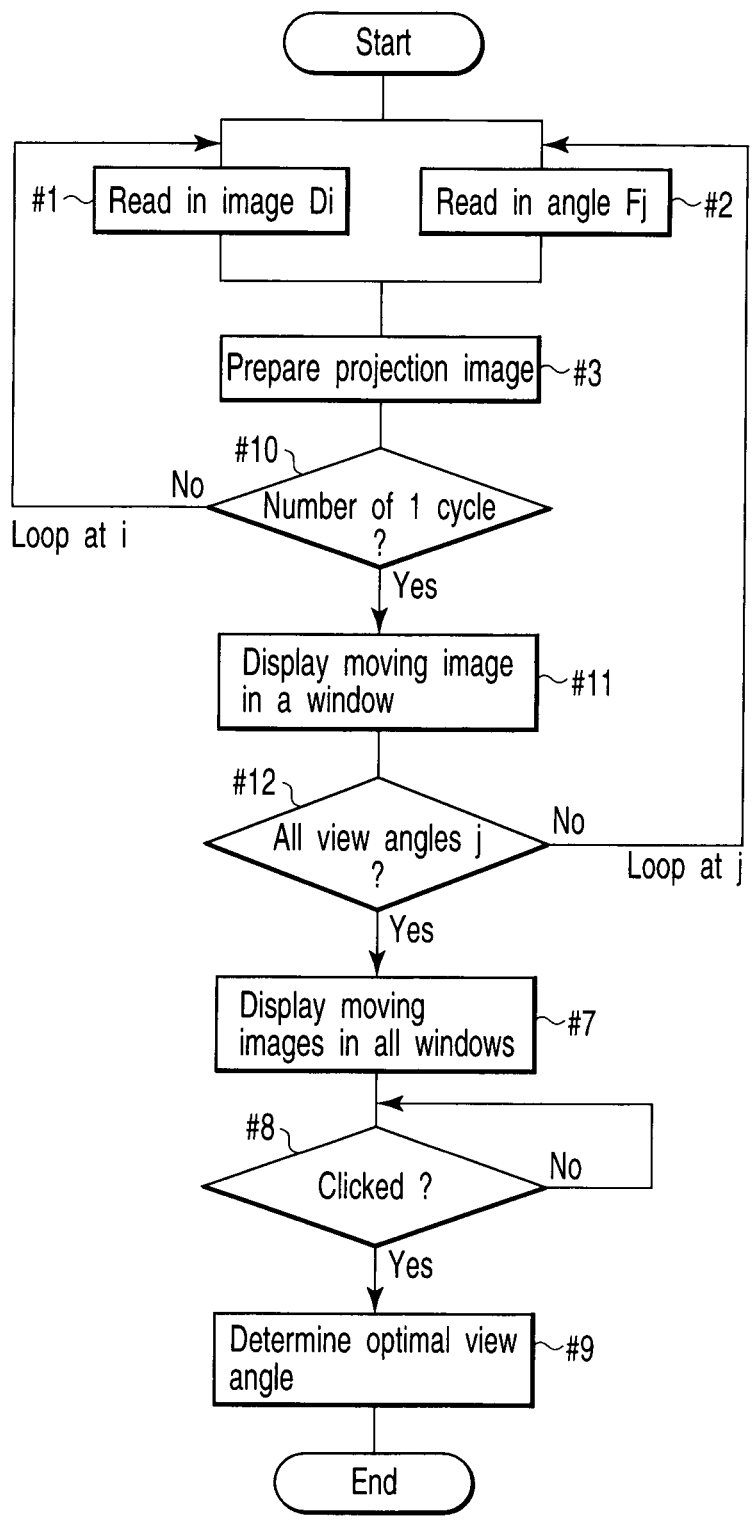
FIG. 7 is a flowchart of the process of preparing a moving three-dimensional image to be displayed on one of the windows of the apparatus.

Now, another specific method of preparing three-dimensional image data $3D_1, 3D_2, 3D_3, \ldots, 3D_9$ will be described by referring to the three-dimensional image data preparing flowchart shown in FIG. 7. The flowchart of FIG. 7 is for producing moving images in the respective windows $W_1$ through $W_9$ sequentially from the three-dimensional image data $3D_1, 3D_2, 3D_3, \ldots, 3D_9$.

Firstly in Step #1, the image data preparing section 17 sequentially reads the four-dimensional image data 4D (x, y, z/t=$i_1$) of a cardiac phase $i_k$ (k=1, 2, 3, \ldots, m) from the image data storage section 13. In Step #2, the image data preparing section 17 reads the nine (j=9) view angles $F_1, F_2, F_3, \ldots, F_9$ from the view angle setting section 16.

Then, in Step #3, the image data preparing section 17 prepares a single image of the projection image data (u, v/t=$i_1$) obtained by projecting in the view angle $F_1$ from the four-dimensional image data 4D (x, y, z/t=$i_1$) of the cardiac phase $i_1$ it reads for the view angle $F_1$. The projection image data (u, v/t=$i_1$) of the single image for the view angle $F_1$ are image data of a still image.

Then in Step #10, the image data preparing section 17 determines if projection image data (u, v/t=$i_1$ through $_m$) of all the cardiac phases $i_k$ (k=1, 2, 3, \ldots, m) are prepared for the view angle $F_1$ or not. In other words, the image data preparing section 17 determines if the number of projection images for the view angle $F_1$ gets to the value necessary for forming a moving image or not. The number of projection images necessary for forming a moving image is the number necessary for continuously displaying a cycle of periodic contracting movement of the object of examination 1 as a moving image. If the object of examination 1 is a coronary artery 1a, the number of projection images necessary for forming a moving image is the number of projection image necessary for continuously displaying a single heartbeat as a moving image.

If it is determined that projection image data (u, v/t=$i_1$ through $_m$) of all the cardiac phases $i_k$ (k=1, 2, 3, \ldots, m) are not prepared for the view angle $F_1$ yet, the image data preparing section 17 returns to Step #1, where it reads the four-dimensional image data 4D (x, y, z/t=$i_2$) of the cardiac phase $i_2$ for the view angle $F_1$ and then, in Step #3, it prepares projection image data (u, v/t=$i_2$) of a single image obtained by projecting in the view angle $F_1$ from the four-dimensional image data 4D (x, y, z/t=$i_2$) of the cardiac phase $i_2$ it reads for the view angle $F_1$. Then, image data preparing section 17 repeats Steps #1 and #3 to prepare projection image data (u, v/t=$i_1$ through $_m$) of projection images obtained by projecting in the view angle $F_1$.

When the number of projection images gets to the value necessary for continuously displaying a heartbeat as a moving image, the image data preparing section 17 completes the operation of preparing three-dimensional image data $3D_1$ of a moving image formed by the projection image data (u, v/t=$i_1$ through $_m$) of all the cardiac phases $i_1$ through $_m$ for the view angle $F_1$. In other words, the three-dimensional image data $3D_1$ of a moving image include image data of a two-dimensional space (u, v) and temporal elements t (=$i_1, 2, 3, \ldots, _m$). The image of the three-dimensional image data $3D_1$ is a moving image of the coronary artery 1a that moves in response to a heartbeat under the condition that the view angle $F_1$ is fixed.

In Step #11, the image data preparing section 17 sends the three-dimensional image data $3D_1$ to the display control section 18. The display control section 18 displays the moving image of the three-dimensional image data $3D_1$ for the view angle $F_1$ in the window $W_1$ on the monitor screen 20a.

Then in Step #12, the image data preparing section 17 determines if the three-dimensional image data $3D_1, 3D_2, 3D_3, \ldots, 3D_9$ of moving images for all the view angles $F_1, F_2, F_3, \ldots, F_9$ are prepared or not. Note that only the three-dimensional image data $3D_1$ of the moving image for the view angle $F_1$ are prepared. Therefore, the image data preparing section 17 returns to Step #2, where it selects the view angle $F_2$ and repeats Steps #3 through #11 to prepare three-dimensional image data $3D_2$ of the moving image for the view angle $F_2$.

As the operation of preparing the three-dimensional image data $3D_2$ of the moving image for the view angle $F_2$ is completed, the image data preparing section 17 sends the three-dimensional image data $3D_2$ to the display control section 18. In Step #11, the display control section 18 displays the moving image of the three-dimensional image data $3D_2$ for the view angle $F_2$ in the window $W_2$ on the monitor screen 20a.

Thereafter, the image data preparing section 17 repeats Steps #2 through #12 to sequentially prepare three-dimensional image data $3D_1$, $3D_2$, $3D_3$, ..., $3D_9$ of moving images for view angles $F_3$, $F_4$, ..., $F_9$. Then, the display control section 18 sequentially displays the moving images in the respective windows $W_3$, $W_4$, ..., $W_9$ on the monitor screen 20a.

When the process of preparing the three-dimensional image data $3D_1$, $3D_2$, $3D_3$, ..., $3D_9$ for all the view angles $F_1$, $F_2$, $F_3$, ..., $F_9$ is completed, the display control section 18 displays the moving images of the three-dimensional image data $3D_1$, $3D_2$, $3D_3$, ..., $3D_9$ for all the view angles $F_1$, $F_2$, $F_3$, ..., $F_9$ in the respective windows $F_1$, $F_2$, $F_3$, ..., $F_9$ on the monitor screen 20a as shown in FIG. 4. The moving images of the three-dimensional image data $3D_1$, $3D_2$, $3D_3$, ..., $3D_9$ are images of the coronary artery 1a that moves in response to a heartbeat under the condition that all the view angles $F_1$ through $F_9$ are fixed. The display of the moving images of the three-dimensional image data $3D_1$, $3D_2$, $3D_3$, ..., $3D_9$ is same as the display of the moving images of the three-dimensional image data $3D_1$, $3D_2$, $3D_3$, ..., $3D_9$ according to the three-dimensional image data preparing flowchart of FIG. 5.

Then, in Step #8, the display control section 18 determines which one of the moving images of the three-dimensional image data $3D_1$ through $3D_9$ for the view angles $F_1$ through $F_9$ being displayed in the respective windows $W_1$ through $W_9$ is to be selected. The surgeon who performs an intravascular intervention operates the mouse of the operation section 19. In response to the mouse operation, pointer P may be placed on the window $W_5$ on the monitor screen 20a and clicked. Then, the display control section 18 receives the click operation. In Step #9, the display control section 18 determines the view angle $F_5$ (0°, 0°) of the window $W_5$ as optimal view angle for the intravascular intervention.

Then, the main control section 12 stores the view angle $F_5$ (0°, 0°) determined as optimal view angle in a memory such as RAM and also transmits it to the medical equipment 11. The medical equipment 11 drives the C arm to rotate in the above-described manner in order to move the X-ray source and the X-ray detector to respective positions that correspond to the view angle $F_5$ (0°, 0°). As a result, it is possible to acquire a moving image of the coronary artery 1a produced by imaging the coronary artery 1a from the view angle $F_5$ (0°, 0°) that is determined as optimal for the intravascular intervention.

Thus, with the above described first embodiment, a plurality of view angles $F_1$ through $F_j$ are selected and set relative to the coronary artery 1a, or the object of examination 1 and a plurality of three-dimensional image data (u, v, t) are prepared from four-dimensional image data 4D (x, y, z, t) of the coronary artery 1a for the plurality of view angles $F_1$ through $F_j$. Then, the moving image of the plurality of three-dimensional image data (u, v, t) 3D showing the coronary artery 1a moving in response to a heartbeat are displayed on the monitor screen 20a under the condition that the plurality of view angles $F_1$ through $F_j$ are fixed.

Thus, it is possible to display the view angles $F_1$ through $F_j$ and the coronary artery 1a moving in response to a heartbeat independently. Then, the surgeon who performs an intravascular intervention can easily and quickly select one of the view angles $F_1$, $F_2$, $F_3$, ..., $F_9$ that is optimal for the intravascular intervention from the moving images showing the coronary artery 1a moving in response to a heartbeat as viewed from a plurality of view angles $F_1$, $F_2$, $F_3$, ..., $F_9$. Thus, the surgeon can find out the optimal view angle for the intravascular intervention as advance information. The selected optimal one of the view angles $F_1$, $F_2$, $F_3$, ..., $F_9$ can avoid any unfavorable effect of some other blood vessel and/or a branched blood vessel overlapping the coronary artery 1a and/or that of foreshortening the coronary artery 1a.

Now, the second embodiment of the present invention will be described by referring to the related ones of the accompanying drawings. Since the configuration of the apparatus is same as those of the apparatus of FIG. 1, only the differences between the two apparatus will be described below.

The operation section 19 typically includes a mouse as switching operation section. As the mouse is operated for a click, the operation section 19 sends a moving image switching signal to the display control section 18 in response to the click.

The display control section 18 temporally sequentially displays the moving images of the three-dimensional image data $3D_3$, $3D_4$, ..., $3D_9$ for the view angles $F_3$, $F_4$, ..., $F_9$ that show the coronary artery 1a moving in response to a heartbeat under the condition that the view angles $F_1$ through $F_9$ are fixed, switching from a view angle to another. More specifically, the display control section 18 switches the display of the moving images of the three-dimensional image data $3D_3$, $3D_4$, ..., $3D_9$ from one to another each time it receives a moving image switching signal. It may be so arranged that the display control section 18 automatically switches the display of the moving images of the three-dimensional image data $3D_3$, $3D_4$, ..., $3D_9$ after showing a moving image for a predetermined time period, for example the time period of a heartbeat.

The program memory 14 stores an image display program to be executed by the main control section 12. The image display program is adapted to temporally sequentially display the moving images of the three-dimensional image data $3D_3$, $3D_4$, ..., $3D_9$ for the view angles $F_3$, $F_4$, ..., $F_9$ on the monitor screen 20a in a switched manner under the condition that the view angles $F_1$ through $F_j$ are fixed.

Now, the image display operation of the apparatus of the second embodiment having the above-described configuration will be described below.

The medical equipment 11 images an object of examination 1 such as the coronary arteries 1a extending around and surrounding a heart showing a heartbeat movement and acquires image data on the object. The four-dimensional data structuring section 15 receives the image data on the object of examination 1 acquired by the medical equipment 11 and structures four-dimensional image data (x, y, z, t) as shown in FIG. 2 from the image data.

On the other hand, the view angle setting section 16 receives the operation input of the operation section by the surgeon who performs an intravascular intervention and selects and sets a plurality of view angles $F_1$ through $F_j$ relative to the coronary artery 1a, or the object of examination 1. The plurality of view angles $F_1$, $F_2$, $F_3$, ..., $F_j$ are set, for example, as nine (j=9) fixed view angles including $F_1$ (RAO 30°, CRA 20°), $F_2$ (0°, CRA 20°), $F_3$ (LAO 50°, CRA 20°), $F_4$ (RAO 30°, 0°), $F_5$ (0°, 0°), $F_6$ (LAO 50°, 0°), $F_7$ (RAO 30°, CAU 30), $F_8$ (0°, CAU 30) and $F_9$ (LAO 50°, CAU 30°).

Figure 8:
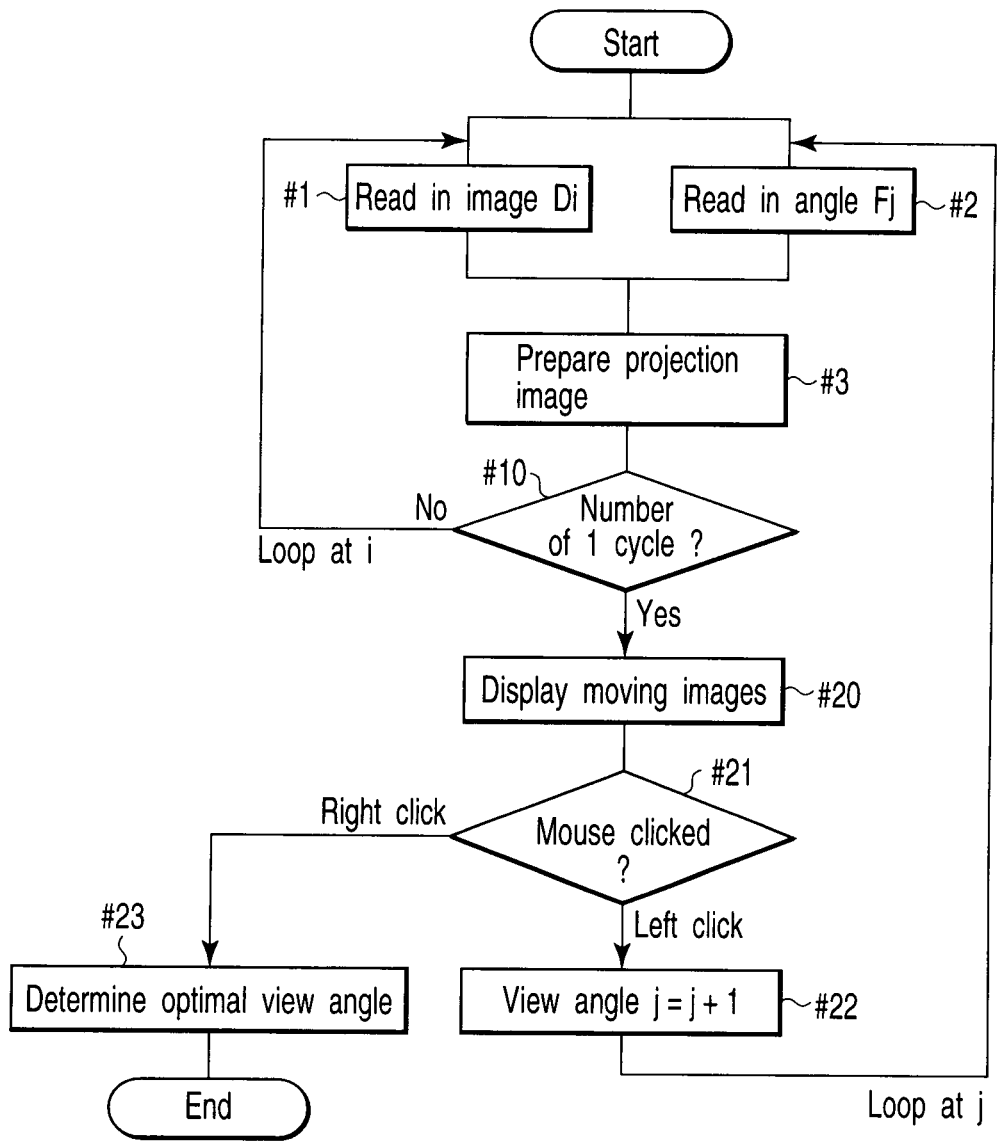
FIG. 8 is a flowchart of the process of preparing three-dimensional image data by a second embodiment of image display apparatus according to the present invention.

Then, the image data preparing section 17 temporally sequentially displays the moving images of the three-dimensional image data $3D_1, 3D_2, 3D_3, \ldots, 3D_9$ for the view angles $F_1, F_2, F_3, \ldots, F_9$ in a switched manner according to the three-dimensional image data preparing flowchart illustrated in FIG. 8. More specifically, in Step #1, the image data preparing section 17 sequentially reads the four-dimensional image data 4D (x, y, z/t=$i_1$) of a cardiac phase $i_k$ (k=1, 2, 3, ..., m) from the image data storage section 13. In Step #2, the image data preparing section 17 reads view angle $F_j$=1, for example, from the view angle setting section 16. Then, in Step #3, the image data preparing section 17 prepares projection image data of the image obtained by projecting in the view angle $F_1$ from the image data it reads.

In Step #3, the image data preparing section 17 prepares projection image data (u, v/t=$i_1$) of a single image obtained by projecting in the view angle $F_1$ from the four-dimensional image data 4D (x, y, z/t=$i_1$) of a cardiac phase $i_1$ read for the view angle $F_1$.

Then, in Step #10, the image data preparing section 17 determines if projection image data (u, v/t=$i_1$ through $_m$) of all the cardiac phases $i_k$ (k=1, 2, 3, ..., m) are prepared for the view angle $F_1$ or not. In other words, the image data preparing section 17 determines if the number of projection images for the view angle $F_1$ gets to the value necessary for forming a moving image or not. If the object of examination 1 is a coronary artery 1a, the number of projection images necessary for forming a moving image is the number of projection image necessary for continuously displaying a single heartbeat as a moving image as described above for the first embodiment.

When the number of projection images of the prepared projection image data gets to the value necessary for continuously displaying a heartbeat as a moving image, the image data preparing section 17 completes the operation of preparing three-dimensional moving images of the three-dimensional image data $3D_1$ for the view angle $F_1$. In other words, the three-dimensional image data $3D_1$ are formed by image data of a two-dimensional space (u, v) and temporal elements t (=$i_1, _2, _3, \ldots, _m$). The image of the three-dimensional image data $3D_1$ is a moving image of the coronary artery 1a that moves in response to a single heartbeat for the fixed view angle $F_1$.

Figure 9:
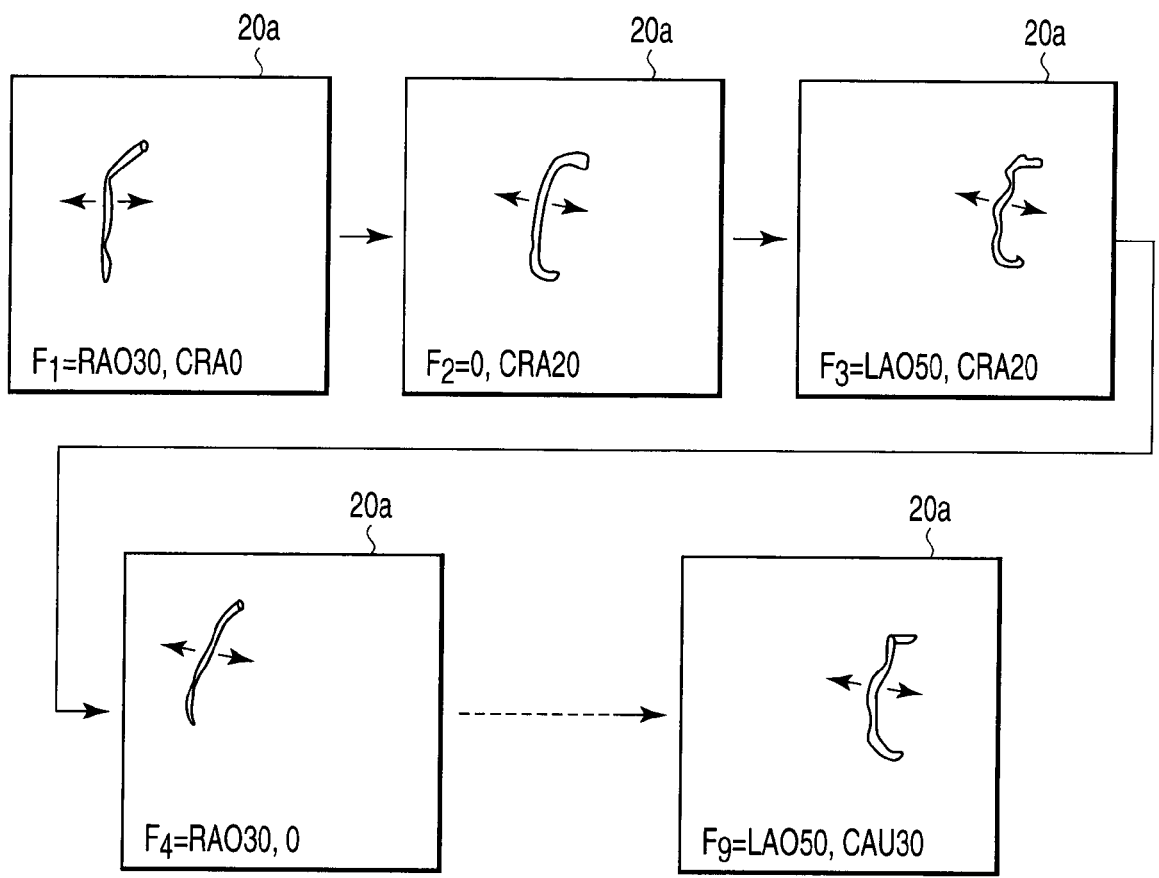
FIG. 9 is a schematic illustration of images that can be displayed on the apparatus of the second embodiment in a switched manner for different view angles.

In Step #20, the image data preparing section 17 sends the three-dimensional image data $3D_1$ to the display control section 18. The display control section 18 displays the moving image of the three-dimensional image data $3D_1$ for the view angle $F_1$ on the monitor screen 20a as shown in FIG. 9. The three-dimensional image data $3D_1$ displays a moving image of the coronary artery 1a that moves in response to a heartbeat under the condition that the view angle $F_1$ is fixed. The arrows in the monitor screen 20a in FIG. 9 indicate the moving directions of the coronary artery 1a that moves in response to the heartbeat.

In Step #21, the image data preparing section 17 determines if the mouse of the operation section 19 is left- or right-clicked or not under this condition. If the mouse is left-clicked, the image data preparing section 17 moves to Step #22, where it increments the suffix of the view angle $F_j$ by "1" and returns to Step #2.

Then, the image data preparing section 17 repeats Steps #1 through #3, #10 and #20 to sequentially read the four-dimensional image data 4D (x, y, z/t=$i_1$) for a cardiac phase $i_k$ (k=1, 2, 3, ..., m) from the image data storage section 13 and also the view angle $F_{j=2}$ from the view angle setting section 16 and prepare a moving image of the three-dimensional image data $3D_2$ for the view angle $F_2$ in a manner as described above.

Then, the image data preparing section 17 sends the three-dimensional image data $3D_2$ to the display control section 18.

The display control section 18 switches the moving image on the monitor screen 20a from that of the three-dimensional image data $3D_1$ for the view angle $F_1$ to that of the three-dimensional image data $3D_2$ for the view angle $F_2$ as shown in FIG. 9. The three-dimensional image data $3D_2$ displays a moving image of the coronary artery 1a that moves in response to a heartbeat under the condition that the view angle $F_2$ is fixed.

Thereafter, as the mouse is left-clicked under the condition that the moving image of the three-dimensional image data $3D_2$ for the view angle $F_2$ is displayed, the image data preparing section 17 moves to Step #22, where it increments the view angle $F_j$ by "1", and then returns to Step #2. Then, the image data preparing section 17 repeats Steps #1 through #3, #10 and #20 and prepares a moving image of the three-dimensional image data $3D_3$ for the view angle $F_3$. Then, the display control section 18 switches the moving image on the monitor screen 20a from that of the three-dimensional image data $3D_2$ for the view angle $F_2$ to that of the three-dimensional image data $3D_3$ for the view angle $F_3$ as shown in FIG. 9.

Thus, each time the mouse is left-clicked, the moving image that is displayed on the monitor screen 20a is switched to that of the three-dimensional image data $3D_4$ for the view angle $F_4$, that of the three-dimensional image data $3D_5, \ldots$, for the view angle $F_5$, that of the three-dimensional image data $3D_9$ for the view angle $F_9$ and that of the three-dimensional image data $3D_1$.

If, on the other hand, it is determined in Step #21 that the mouse of the operation section 19 is right-clicked, the image data preparing section 17 moves to Step #23, where it determines that the view angle $F_j$ of the three-dimensional image data $3D_j$ of the moving image that is being displayed on the monitor screen 20a at the time when the mouse is right-clicked is an optimal view angle. If, for instance, the moving image of the three-dimensional image data $3D_1$ for the view angle $F_1$ is being displayed on the monitor screen 20a at the time when the mouse is right-clicked, the image data preparing section 17 determines that the view angle $F_1$ is an optimal view angle.

Then, the main control section 12 stores the view angle $F_1$ that is determined as optimal view angle (RAO 30°, CRA 20°) in a memory such as RAM and also transmits it to the medical equipment 11. The medical equipment 11 then drives the C arm to rotate in the above-described manner in order to move the X-ray source and the X-ray detector to respective positions that correspond to the view angle $F_1$(RAO 30°, CRA 20°). As a result, it is possible to acquire a moving image of the coronary artery 1a produced by imaging the coronary artery 1a from the view angle $F_1$ (RAO 30°, CRA 20°) optimal for the intravascular intervention.

Thus, with the above-described second embodiment, each time the mouse is left-clicked, the moving image that is displayed on the monitor screen 20a is switched to that of the three-dimensional image data $3D_1$ for the view angle $F_1$, that of the three-dimensional image data $3D_2$ for the view angle $F_2, \ldots$, that of the three-dimensional image data $3D_9$ for the view angle $F_9$ and that of the three-dimensional image data $3D_1$. It will be clear that this embodiment provides advantages similar to those of the first embodiment.

As described above, the moving image that is displayed on the monitor screen 20a is switched to that of the three-dimensional image data $3D_1$ for the view angle $F_1$, that of the three-dimensional image data $3D_2$ for the view angle $F_2, \ldots$, that of the three-dimensional image data $3D_9$ for the view angle $F_9$ and that of the three-dimensional image data $3D_1$ each time the mouse is left-clicked in the second embodiment. However, the present invention is by no means limited to such an arrangement. For example, it may alternatively be so arranged that a switching icon is displayed on the monitor screen 20a and a pointer P is arranged on the icon so that, each time the mouse is left-clicked, the moving image that is displayed on the monitor screen 20a is switched to that of the three-dimensional image data $3D_1$ for the view angle $F_1$, that of the three-dimensional image data $3D_2$ for the view angle $F_2$, . . . , that of the three-dimensional image data $3D_9$ for the view angle $F_9$ and that of the three-dimensional image data $3D_1$. Still alternatively, a keyboard, a touch panel or a joystick may be used for switching the moving image.

In the above-described second embodiment, each time the mouse is left-clicked, the image data preparing section 17 reads the four-dimensional image data 4D (x, y, z/t=$i_1$) of a cardiac phase $i_k$ (k=1, 2, 3, . . . , m) from the image data storage section 13 and also a view angle $F_j$ from the view angle setting section 16 to prepare a moving image of the three-dimensional image data $3D_2$ for the view angle $F_2$. However, the present invention is by no means limited to such an arrangement. It may alternatively be so arranged that moving images of the three-dimensional image data $3D_1$, $3D_2$, $3D_3$, . . . , $3D_9$ for all the view angles $F_1$, $F_2$, $F_3$, . . . , $F_9$ are prepared in advance in the background and stored in the image data storage section 13 so that the moving image of the three-dimensional image data $3D_1$, $3D_2$, $3D_3$, . . . , or $3D_9$ is read out and displayed on the monitor screen 20a each time the mouse is left-clicked.

Now, the third embodiment of the present invention will be described below by referring to the related ones of the accompanying drawings. Note that the components same as those of FIG. 1 are denoted respectively by the same reference symbols.

Figure 10:
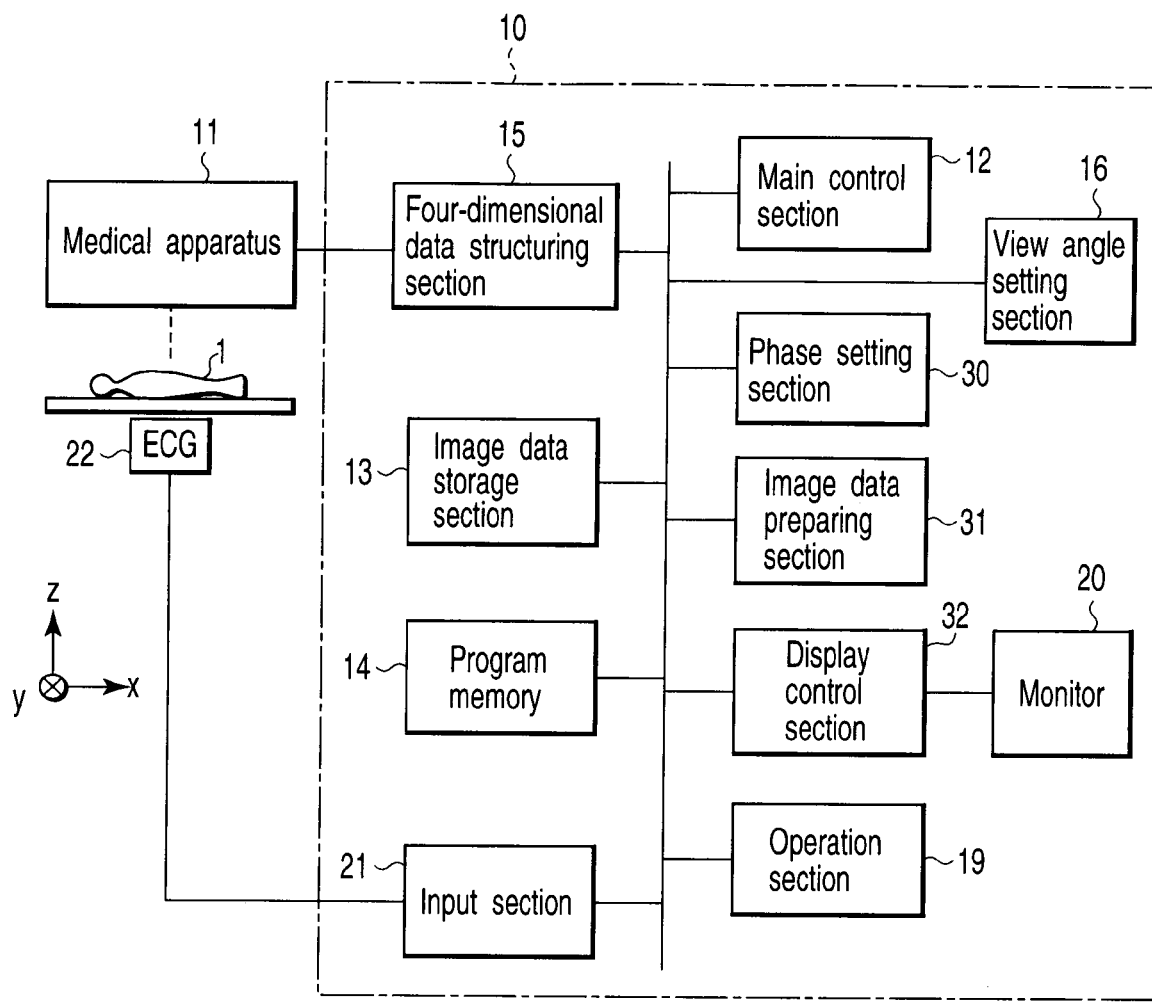
FIG. 10 is a schematic block diagram of a third embodiment of image display apparatus according to the present invention.
Figure 11:
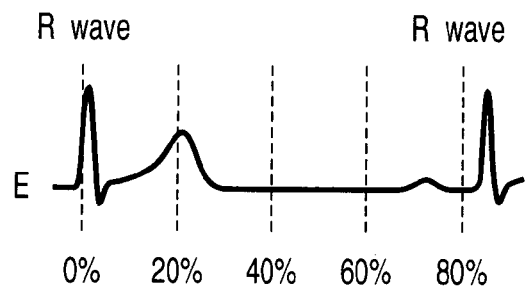
FIG. 11 is a schematic illustration of the waveform of an electrocardiogram acquired by the apparatus according to the third embodiment.

FIG. 10 is a schematic block diagram of the third embodiment of image display apparatus according to the present invention. Referring to FIG. 10, the image display apparatus main body 10 is provided with a phase setting section 30. The phase setting section 30 operates according to the command issued from the main control section 12. The phase setting section 30 selects and sets a plurality of cardiac phases that show a heartbeat movement as object of examination 1. The cardiac phases are selected from the electrocardiogram waveform E acquired by means of an electrocardiograph 22 as $i_k$ (k=1, 2, 3, . . . , m) and fixed to $i_{k=1}$ (0%), $i_{k=2}$ (20%), $i_{k=3}$ (40%), $i_{k=4}$ (60%) and $i_{k=5}$ (80%), for example, as shown in FIG. 11. To be accurate, optimal values for the surgeon to perform an intravascular intervention are selected and fixed as cardiac phases $i_k$.

The image data preparing section 31 reads out the four-dimensional image data 4D (x, y, z, t) stored in the image data storage section 13. The image data preparing section 31 prepares a plurality of three-dimensional image data (r, s) $3D_k$, continuously shifting the view angle RAO, LAO relative to the heart for each of the cardiac phases $i_k$ that are selected and fixed by the phase setting section 30, from the three-dimensional image data 4D (x, y, z, t). Each three-dimensional image data $3D_k$ include image data of a two-dimensional space (r, s) and temporal elements t (=$i_{1, 2, 3, \ldots, m}$).

The display control section 32 displays moving images of the three-dimensional image data $3D_k$ obtained by selecting view angle CRA0, CAU0 and continuously shifting RAO, LAO on the monitor screen 20a. The display control section 32 displays rotating images of the three-dimensional image data $3D_{10}$, $3D_{11}$, $3D_{12}$, $3D_{13}$, $3D_{14}$ for the respective cardiac phases of 0%, 20%, 40%, 60% and 80%, synchronously changing their view angles $F_j$, on the monitor screen 20a.

Each of the three-dimensional image data $3D_{10}$, $3D_{11}$, $3D_{12}$, $3D_{13}$, $3D_{14}$ includes image data of a two-dimensional space (u, v) and temporal elements t (=$i_{1, 2, 3, \ldots, m}$).

Figure 12:
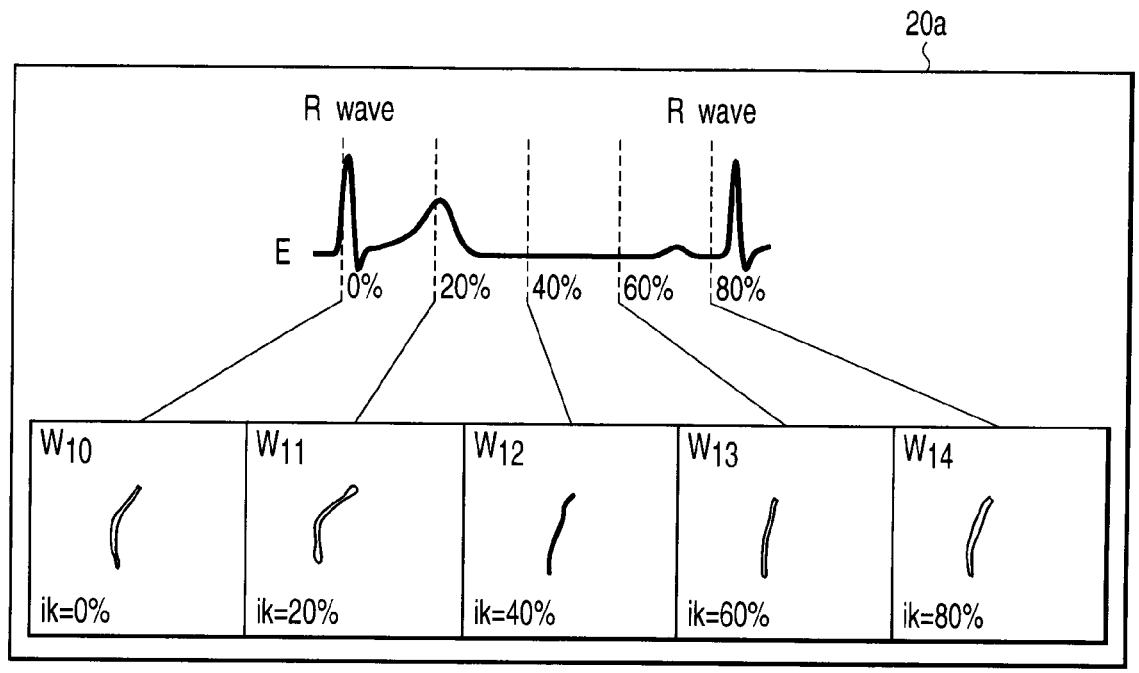
FIG. 12 is an exemplary image of that three-dimensional image data that can be obtained by continuously shifting the view angle for each of the cardiac phases and displayed as synopsis on the monitor screen of the apparatus according to the third embodiment.

FIG. 12 shows how each of the moving images of the three-dimensional image data $3D_{10}$, $3D_{11}$, $3D_{12}$, $3D_{13}$, $3D_{14}$ in the respective cardiac phases $i_k$ that are displayed as synopsis appears when the view angle RAO, LAO is continuously shifted. A plurality of windows W such as windows $W_{10}$ through $W_{14}$ is shown on the monitor screen 20a. The windows $W_{10}$ through $W_{14}$ respectively display the rotating images of the three-dimensional image data $3D_{10}$, $3D_{11}$, $3D_{12}$, $3D_{13}$, $3D_{14}$ in the cardiac phases $i_k$.

The moving images of the three-dimensional image data $3D_{10}$, $3D_{11}$, $3D_{12}$, $3D_{13}$, $3D_{14}$ are those obtained by selecting view angle CRA0, CAU0 and continuously shifting RAO, LAO. The rate of shifting RAO, LAO may be arbitrarily selected. For example, it may be made to agree with the heartbeat rate. The view angle $F_j$ is rotated, for example, as $F_{j=10}$ (RAO 0, CRA 0)→$F_{j=11}$ (RAO 30°, CRA 0)→$F_{j=12}$ (RAO 30°, CAU 30°)→$F_{j=13}$ (RAO 0, CAU 30°)→$F_{j=14}$ (LAO 30°, CAU 30°)→$F_{j=15}$ (LAO 30°, CRA 30°)→$F_{j=16}$ (RAO 30°, CRA 30°)→$F_{j=17}$ (RAO 30°, CRA 0).

The program memory 14 stores the image display program to be executed by the main control section 12. The image display program is designed to select and fix the cardiac phases for the heartbeat movement, or the object of examination 1, prepare a plurality of three-dimensional image data (r, s) $3D_k$, continuously shifting view angle RAO, LAO, relative to the heart for each of a plurality of cardiac phases $i_k$ from four-dimensional image data 4D (x, y, z, t) and displaying the rotating images of the plurality of three-dimensional image data $3D_k$ obtained by selecting view angle CRA 0, CAU 0 but continuously shifting RAO, LAO under the condition that the cardiac phases $i_k$ are fixed.

Now, the image display operation of the apparatus of the third embodiment having the above-described configuration will be described below.

The medical equipment 11 images an object of examination 1 such as the coronary arteries 1a extending around and surrounding a heart showing a heartbeat movement and acquires image data on the object. The four-dimensional data structuring section 15 receives the image data on the object of examination 1 acquired by the medical equipment 11 and structures four-dimensional image data 4D (x, y, z, t) as shown in FIG. 2 from the image data.

On the other hand, the phase setting section 30 selects a plurality of cardiac phases $i_k$ that show a heartbeat movement, or the object of examination 1. The cardiac phases $i_k$ are selected from the electrocardiogram waveform acquired by means of an electrocardiograph 22 as $i_k$ (k=1, 2, 3, . . . , m) and fixed to 0%, 20%, 40%, 60% and 80%, for example, as shown in FIG. 11. To be accurate, optimal values for the surgeon to perform an intravascular intervention are selected and fixed as cardiac phases $i_k$.

Then, the image data preparing section 31 reads out the four-dimensional image data 4D (x, y, z, t) stored in the image data storage section 13 and prepares a plurality of three-dimensional image data $3D_1$, $3D_{11}$, $3D_{12}$, $3D_{13}$, $3D_{14}$ by selecting view angle CRA0, CAU0 but continuously shifting the view angle RAO, LAO relative to the heart for each of the cardiac phases $i_k$ that are selected and fixed by the phase setting section 30, from the three-dimensional image data 4D (x, y, z, t).

Figure 14:
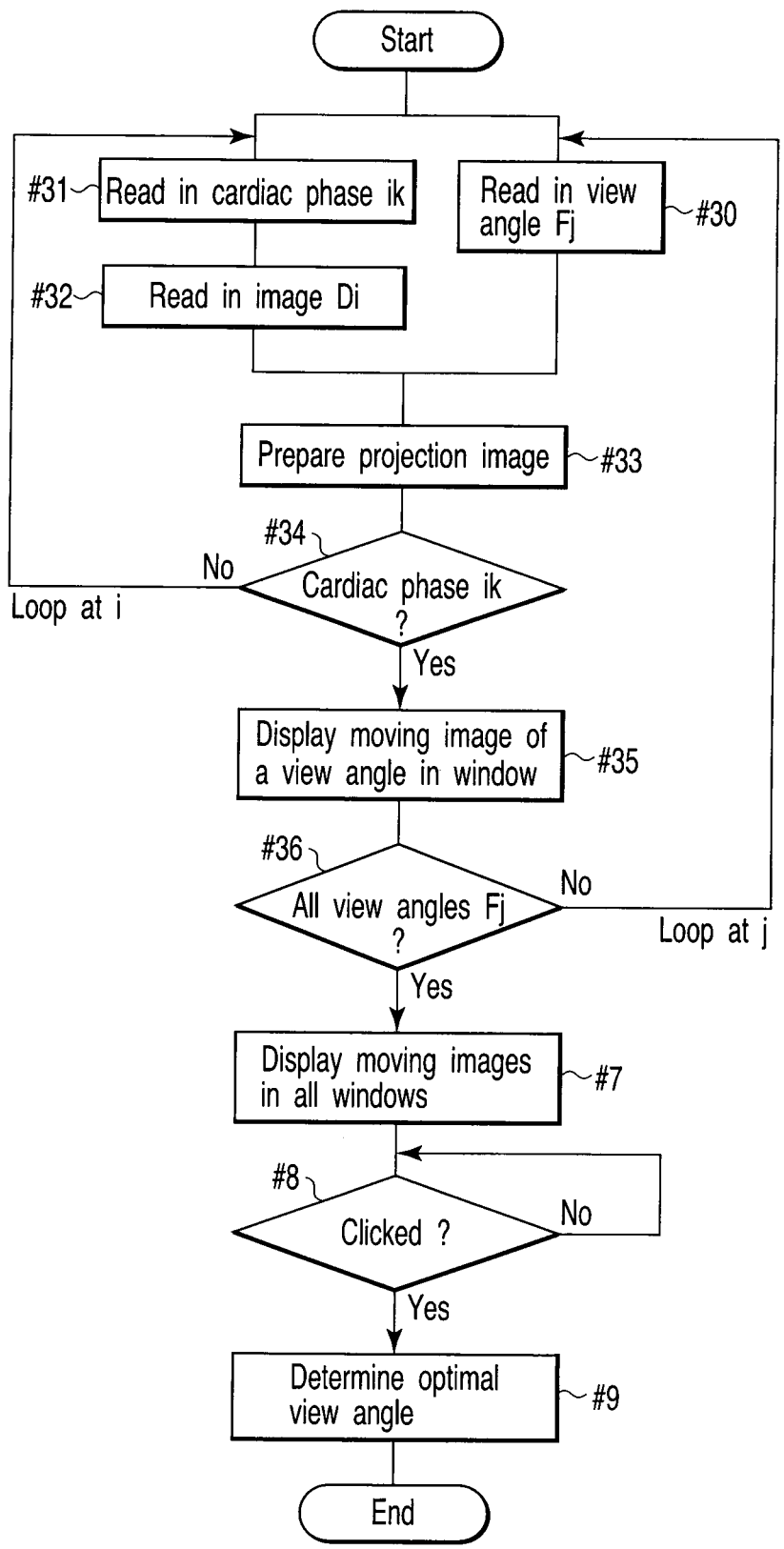
FIG. 14 is a flowchart of the process of preparing three-dimensional data of the images to be displayed in the respective windows of the apparatus according to the third embodiment.

A specific method of preparing the three-dimensional image data $3D_{10}$, $3D_{11}$, $3D_{12}$, $3D_{13}$, $3D_{14}$ will be described below by referring to the three-dimensional image data preparing flowchart of FIG. 14. The flowchart of FIG. 14 shows that the three-dimensional image data $3D_{10}$, $3D_{11}$, $3D_{12}$, $3D_{13}$, $3D_{14}$ of the moving images to be displayed in the respective windows $W_{10}$ through $W_{14}$ are prepared simultaneously.

Firstly in Step #30, the image data preparing section 31 reads the view angle j from the view angle setting section 16. The view angle j may be, for example, $F_{j=10}$ (RAO 0, CRA 0), $F_{j=11}$ (RAO 30°, CRA 0), $F_{j=12}$ (RAO 30°, CAU 30), $F_{j=13}$ (RAO 0, CAU 30°), $F_{j=14}$ (LAO 30°, CAU 30°), $F_{j=15}$ (LAO 30°, CRA 30°), $F_{j=16}$ (RAO 30°, CRA 30°), $F_{j=17}$ (RAO 30°, CRA 0).

At the same time in Step #31, the image data preparing section 31 typically reads five (k=5) cardiac phases $i_k$ (k=1, 2, 3, ..., m) from the phase setting section 30. The five cardiac phases may include $i_{k=1}$ (0%), $i_{k=2}$ (20%), $i_{k=3}$ (40%), $i_{k=4}$ (60%) and $i_{k=5}$ (80%).

Then in Step #32, the image data preparing section 31 reads, for example, the four-dimensional image data 4D (x, y, z/$i_1$) for the cardiac phase $i_{k=1}$ (=0%) from the image data storage section 13.

Then in Step #33, the image data preparing section 31 prepares projection image data (u, v/t=$i_1$) of a single projection image obtained by projecting in the view angle $F_{j=10}$ (RAO 0, CRA 0) from the four-dimensional image data 4D (x, y, z/$i_1$) for the cardiac phase $i_{k=1}$ (=0%). The single projection image of the projection image data (u, v/t=$i_1$) for the view angle $F_{j=10}$ (RAO 0, CRA 0) is a still image.

Then in Step #34, the image data preparing section 31 determines if projection image data (u, v/t=$i_1$ through $_5$) for all the cardiac phases $i_k$ including, for example, $i_{k=1}$ (0%), $i_{k=2}$ (20%), $i_{k=3}$ (40%), $i_{k=4}$ (60%) and $i_{k=5}$ (80%) are prepared or not.

If it is determined that projection image data (u, v/t=$i_1$ through $_5$) for all the cardiac phases $i_k$ are not prepared yet, the image data preparing section 31 returns to Step #32 and reads the four-dimensional image data 4D (x, y, z/$i_1$) for the cardiac phase $i_{k=2}$ (=20%). Then in Step #33, the image data preparing section 31 prepares projection image data (u, v/t $i_1$) of a single projection image obtained by projecting in the view angle $F_{j=10}$ (RAO 0, CRA 0) from the four-dimensional image data 4D (x, y, z/$i_1$) for the cardiac phase $i_{k=2}$ (=20%).

Then, the image data preparing section 31 repeats Steps #32 through #34 in the same manner to sequentially read the four-dimensional image data 4D (x, y, z/$i_1$) for the cardiac phases $i_{k=3}$ (40%), $i_{k=4}$ (60%) and $i_{k=5}$ (80%) and prepare projection image data (u, v/t=$i_3$ through $_5$) of projection images projected in the view angle $F_{j=10}$ (RAO 0, CRA 0) from the four-dimensional image data 4D (x, y, z/$i_3$ through $_5$) for the cardiac phases $i_{k=3}$ (40%), $i_{k=4}$ (60%) and $i_{k=5}$ (80%).

When projection image data (u, v/t=$i_1$ through $_5$) for all the cardiac phases $i_{k=5}$ are prepared, the image data preparing section 31 sends the projection image data (u, v/t=$i_1$ through $_5$) for the cardiac phases $i_{k=3}$ (40%), $i_{k=4}$ (60%) and $i_{k=5}$ (80%) in the single view angle $F_{j=10}$ (RAO 0, CRA 0) to display control section 32 in Step #34.

The display control section 32 displays the projection images of the projection image data for the cardiac phases $i_k$ (=0%, 20%, 40%, 60%, 80%) respectively on the windows $W_{10}$ through $W_{14}$ on the monitor screen 20a as shown in FIG. 12. The projection images of the projection image data that are displayed in the respective windows $W_{10}$ through $W_{14}$ on the monitor screen 20a at this time are still images.

Then in Step #36, the image data preparing section 31 determines if the projection image data for all the view angles $F_j$ including $F_{j=10}$ (RAO 0, CRA 0), $F_{j=11}$ (RAO 30°, CRA 0), $F_{j=12}$ (RAO 30°, CAU 30), $F_{j=13}$ (RAO 0, CAU 30°), $F_{j=14}$ (LAO 30°, CAU 30°), $F_{j=15}$ (LAO 30°, CRA 30), $F_{j=16}$ (RAO 30°, CRA 30°), $F_{j=17}$ (RAO 30°, CRA 0) are prepared for each of the cardiac phases $i_k$ (=0%, 20%, 40%, 60%, 80%) or not.

If it is determined that projection image data for all the view angles $F_j$ are not prepared yet, the image data preparing section 31 returns to Step #30, where it reads the next view angle $F_j$ (RAO 30°, CRA 0) and then moves to Step #33.

In this way, the image data preparing section 31 repeats Steps #30 through #36 and prepares projection image data (u, v/t=$i_1$ through $_5$) all the view angles $F_j$ including $F_{j=10}$ (RAO 0, CRA 0), $F_{j=11}$ (RAO 30°, CRA 0), $F_{j=12}$ (RAO 30°, CAU 30°), $F_{j=13}$ (RAO 0, CAU 30°), $F_{j=14}$ (LAO 30°, CAU 30), $F_{j=15}$ (LAO 30°, CRA 30°), $F_{j=16}$ (RAO 30°, CRA 30°), $F_{j=17}$ (RAO 30°, CRA 0) for each of the cardiac phases $i_{k=3}$ (40%), $i_{k=4}$ (60%) and $i_{k=5}$ (80%). As a result, the image data preparing section 31 can prepare a plurality of three-dimensional image data $3D_{10}$, $3D_{11}$, $3D_{12}$, $3D_{13}$, $3D_{14}$ by selecting view angle CRA 0, CAU 0 but continuously shifting RAO, LAO relative to the heart for each of the cardiac phases $i_k$.

As the process of preparing moving images of all the three-dimensional image data $3D_{10}$, $3D_{11}$, $3D_{12}$, $3D_{13}$, $3D_{14}$ for each of the cardiac phases $i_k$ (=0%, 20%, 40%, 60%, 80%) is completed, the image data preparing section 31 sends the three-dimensional image data $3D_{10}$, $3D_{11}$, $3D_{12}$, $3D_{13}$, $3D_{14}$ for each of the cardiac phases $i_k$ to the display control section 18.

In Step #7, the display control section 32 displays the moving images of the three-dimensional image data $3D_{10}$, $3D_{11}$, $3D_{12}$, $3D_{13}$, $3D_{14}$ for each of the cardiac phases $i_k$ (=0%, 20%, 40%, 60%, 80%) respectively in the windows $W_{10}$ through $W_{14}$ on the monitor screen 20a as shown in FIG. 12. More specifically, the display control section 32 displays the moving images of the three-dimensional image data $3D_{10}$, $3D_{11}$, $3D_{12}$, $3D_{13}$, $3D_{14}$ for each of the cardiac phases $i_k$ (=0%, 20%, 40%, 60%, 80%) in the respective windows $W_{10}$ through $W_{14}$ synchronously in terms of the view angle $F_j$.

Figure 13:
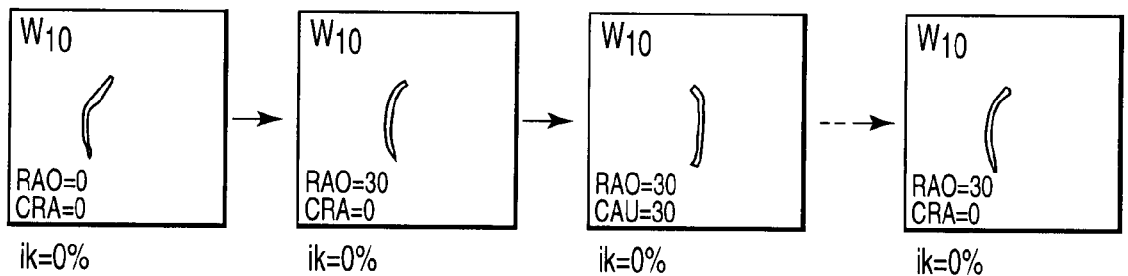
FIG. 13 is a schematic illustration of a moving three-dimensional image of three-dimensional image data that can be displayed on the monitor screen of the apparatus according to the third embodiment.

FIG. 13 illustrates the moving image of the three-dimensional image data $3D_{10}$ for the cardiac phase Public key (=0%) displayed in the window $W_{10}$. The moving image of the three-dimensional image data $3D_{10}$ is a moving image obtained by shifting the view angle $F_j$, for example, in the order of $F_{j=10}$ (RAO 0, CRA 0)→$F_{j=11}$ (RAO 30°, CRA 0)→$F_{j=12}$ (RAO 30°, CAU 30°)→$F_{j=13}$ (RAO 0, CAU 30°)→$F_{j=14}$ (LAO 30°, CAU 30)→$F_{j=15}$ (LAO 30°, CRA 30°)→$F_{j=16}$ (RAO 30°, CRA 30°)→$F_{j=17}$ (RAO 30°, CRA 0). The display control section 32 receives the electrocardiogram signal output from the electrocardiograph 22 as input and displays the electrocardiogram waveform E in the monitor screen 20a.

Then in Step #8, the display control section 32 determines which one of the moving images of the three-dimensional image data $3D_{10}$, $3D_{11}$, $3D_{12}$, $3D_{13}$, $3D_{14}$ for each of the view angles $i_k$ (=0%, 20%, 40%, 60%, 80%) being displayed in the respective windows $W_{10}$ through $W_{14}$ is to be selected. The surgeon who performs an intravascular intervention operates the mouse of the operation section 19. In response to the mouse operation, pointer P may be placed on the window $W_{10}$ on the monitor screen 20a and clicked. Then, the display control section 32 receives the click operation. In Step #9, the display control section 32 determines the view angle of window $W_{10}$, or CRA 0 CAU 0 and RAO 30° CAU 30° as optimal view angle for the intravascular intervention.

Then, the main control section 12 stores the view angle RAO 30° CAU 30° determined as optimal view angle in a memory such as RAM and also transmits it to the medical equipment 11. The medical equipment 11 drives the C arm to rotate in the above described manner in order to move the X-ray source and the X-ray detector to respective positions that correspond to the view angle RAO 30° CAU 30°. As a result, it is possible to acquire a moving image of the coronary artery $1a$ produced by imaging the coronary artery $1a$ from the view angle RAO 30° CAU 30° that is determined as optimal for the intravascular intervention.

Figure 15:
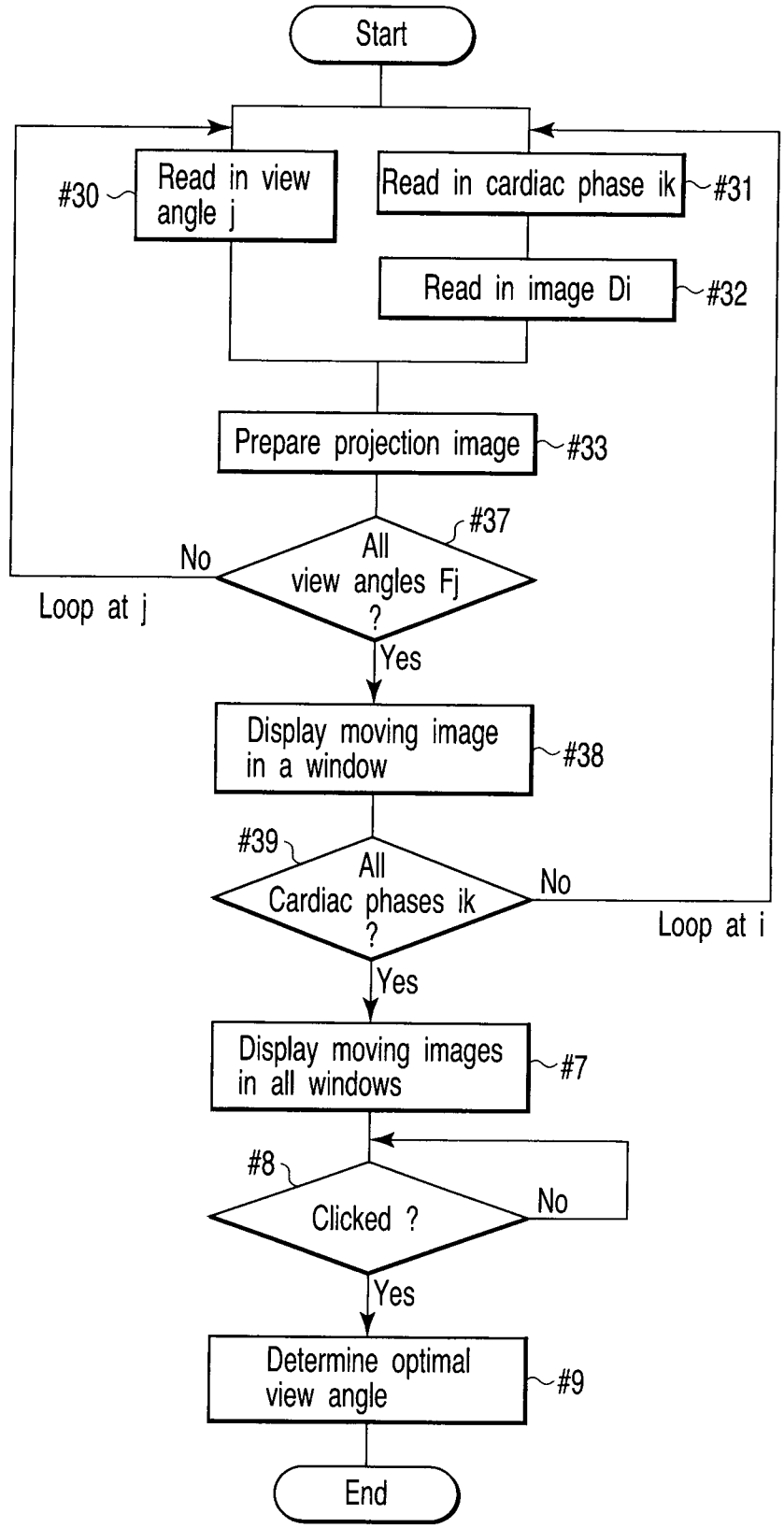
FIG. 15 is a flowchart of the process of preparing three-dimensional data of each moving image to be displayed in one of the windows of the apparatus according to the third embodiment.

Now, another specific method of preparing three-dimensional image data $3D_{10}$, $3D_{11}$, $3D_{12}$, $3D_{13}$, $3D_{14}$ will be described by referring to the three-dimensional image data preparing flowchart of FIG. 15. The process of the flowchart of FIG. 15 will be repeated for the moving images of the three-dimensional image data $3D_{10}$, $3D_{11}$, $3D_{12}$, $3D_{13}$, $3D_{14}$ to be displayed in the respective windows $W_{10}$ through $W_{14}$.

Firstly in Step #30, the image data preparing section 31 reads the view angles $F_j$ from the view angle setting section 16. The view angles $F_j$ may include, for instance, $F_{j=10}$ (RAO 0, CRA 0), $F_{j=11}$ (RAO 30°, CRA 0), $F_{j=12}$ (RAO 30°, CAU 30), $F_{j=13}$ (RAO 0, CAU 30°), $F_{j=14}$ (LAO 30°, CAU 30°), $F_{j=15}$ (LAO 30°, CRA 30°), $F_{j=16}$ (RAO 30°, CRA 30°), $F_{j=17}$ (RAO 30°, CRA 0).

At the same time in Step #31, the image data preparing section 31 reads, for example, five (k=5) cardiac phases $i_k$ (k=1, 2, 3, . . . , m) including $i_{k=1}$ (0%), $i_{k=2}$ (20%), $i_{k=3}$ (40%), $i_{k=4}$ (60%) and $i_{k=5}$ (80%) from the phase setting section 30.

Then in Step #32, the image data preparing section 31 reads the four-dimensional image data 4D (x, y, z/$i_1$), for example, for the cardiac phase $i_1$ (=0%) from the image data storage section 13.

Subsequently in Step #33, the image data preparing section 31 prepares projection image data (u, v/t=$i_1$) of a single image obtained by projecting in the view angle $F_{j=10}$ (RAO 0, CRA 0) from the four-dimensional image data 4D (x, y, z/$i_1$).

Then in Step #37, the image data preparing section 31 determines if projection image data (u, v/t=$i_1$) of, for example, $F_{j=10}$ (RAO 0, CRA 0), $F_{j=11}$ (RAO 30°, CRA 0), $F_{j=12}$ (RAO 30°, CAU 30°), $F_{j=13}$ (RAO 0, CAU 30°), $F_{j=14}$ (LAO 30°, CAU 30), $F_{j=15}$ (LAO 30°, CRA 30°), $F_{j=16}$ (RAO 30°, CRA 30°), $F_{j=17}$ (RAO 30°, CRA 0) are prepared for all the view angles $F_j$ in the cardiac phase $i_1$ (=0%) or not.

If it is determined that projection image data (u, v/t=$i_1$) are not prepared yet for all the view angles $F_j$ in the cardiac phase $i_1$ (=0%), the image data preparing section 31 returns to Step #30, where it selects the next view angle $F_{j=11}$ (RAO 30°, CRA 0). Then in Step #33, the image data preparing section 31 prepares projection image data (u, v/t=$i_1$) of a single image obtained by projecting in the view angle $F_{j=11}$ (RAO 30°, CRA 0) from the four-dimensional image data 4D (x, y, z/$i_1$).

Thereafter, the image data preparing section 31 repeats Steps #30 through #33 and #37 to prepare projection image data (u, v/t=$i_1$) of all the view angles $F_j$ including, for example, $F_{j=10}$ (RAO 0, CRA 0), $F_{j=11}$ (RAO 30°, CRA 0), $F_{j=12}$ (RAO 30°, CAU 30°), $F_{j=13}$ (RAO 0, CAU 30°), $F_{j=14}$ (LAO 30°, CAU 30°), $F_{j=15}$ (LAO 30°, CRA 30°), $F_{j=16}$ (RAO 30°, CRA 30), $F_{j=17}$ (RAO 30°, CRA 0) in the cardiac phase $i_1$ (=0%).

As projection image data (u, v/t=$i_1$) of all the view angles $F_j$ (j=10 through 17) are prepared in the cardiac phase $i_1$ (=0%), the image data preparing section 31 sends the three-dimensional image data $3D_{10}$ formed by using the projection image data (u, v/t=$i_1$) of all the view angles $F_j$ (j=10 through 17) in the cardiac phase $i_1$ (=0%) to the display control section 32 in Step #38. Then, the display control section 32 displays the rotating image of the three-dimensional image data $3D_{10}$ of the coronary artery $1a$ from the view angles $F_j$ (J=10 through j=17) in the cardiac phase $i_1$ (=0%) in the window $W_{10}$ on the monitor screen $20a$ as shown in FIG. 12.

Then, in Step #39, the image data preparing section 31 determines if projection image data (u, v/t=$i_{k=1\ through\ 5}$) of the coronary artery $1a$ in all the cardiac phases $i_k$ (=0%, 20%, 40%, 60%, 80%) are prepared or not. If it is determined that projection image data (u, v/t=$i_{k=1\ through\ 5}$) in all the cardiac phases $i_k$ (=0%, 20%, 40%, 60%, 80%) are not prepared yet, the image data preparing section 31 returns to Step #31, where it reads the four-dimensional image data 4D (x, y, z/$i_1$) of the cardiac phase $i_{k=2}$ (=20%) from the phase setting section 30. In Step #32, the image data preparing section 31 reads the four-dimensional image data 4D (x, y, z/$i_1$) of the cardiac phase $i_{k=2}$ (=20%) from the image data storage section 13.

Then, the image data preparing section 31 repeats Steps #30 through #33 and #37 through #39 and sends the three-dimensional image data $3D_{11}$ including the projection image data (u, v/t=$i_2$) of the view angles $F_j$ (j=10 through 17) in the cardiac phase $i_{k=2}$ (=20%) to the display control section 32. The display control section 32 displays the rotating image of the projection image data (u, v/t=$i_2$), for example, of the view angles $F_j$ (j=10 through 17) of the coronary artery $1a$ in the cardiac phase $i_{k=2}$ (=0%) in the window $W_{11}$ on the monitor screen $20a$ as shown in FIG. 12.

Thereafter, the image data preparing section 31 repeats Steps #30 through #33 and #37 through #39 in the same manner and sends the three-dimensional image data $3D_{12}$, $3D_{13}$, $3D_{14}$ including the projection image data (u, v/t=$i_3$ through $_5$) of all the view angles $F_j$ (j=10 through 17) in each of the cardiac phases $i_{k=3}$ (=40%), $i_{k=4}$ (=60%) and $i_{k=5}$ (=80%) to the display control section 32.

The display control section 32 displays the rotating images of the projection image data (u, v/t=$i_3$ through $_5$) of the view angles $F_j$ (j=10 through j=17) of the coronary artery $1a$ in the cardiac phases $i_{k=3}$ (=40%), $i_{k=4}$ (=60%), $i_{k=5}$ (=80%) respectively in the windows $W_{12}$ through $W_{14}$ on the monitor screen $20a$. Thus in Step #7, the display control section 32 synchronously displays the moving images of the three-dimensional image data $3D_{10}$, $3D_{11}$, $3D_{12}$, $3D_{13}$, $3D_{14}$ in the cardiac phases $i_k$ (=0%, 20%, 40%, 60%, 80%) respectively in the windows $W_{10}$ through $W_{14}$ on the monitor screen $20a$. The display control section 32 also displays the electrocardiogram waveform E on the monitor screen $20a$.

Then in Step #8, the display control section 32 determines which one of the moving images of the three-dimensional image data $3D_{10}$, $3D_{11}$, $3D_{12}$, $3D_{13}$, $3D_{14}$ for each of the view angles $i_k$ (=0%, 20%, 40%, 60%, 80%) being displayed in the respective windows $W_{10}$ through $W_{14}$ is to be selected. The surgeon who performs an intravascular intervention operates the mouse of the operation section 19. In response to the mouse operation, pointer P may be placed on the window $W_{10}$ on the monitor screen $20a$ and clicked. Then, the display control section 32 receives the click operation. In Step #9, the display control section 32 determines the view angle of window $W_{10}$, or CRA 0 CAU 0 and RAO 30° CAU 30° as optimal view angle for the intravascular intervention.

Then, the main control section 12 stores the view angle RAO 30° CAU 30° determined as optimal view angle in a memory such as RAM and also transmits it to the medical equipment 11. The medical equipment 11 drives the C arm to rotate in the above described manner in order to move the X-ray source and the X-ray detector to respective positions that correspond to the view angle RAO 30° CAU 30°. As a result, it is possible to acquire a moving image of the coronary artery $1a$ produced by imaging the coronary artery $1a$ from the view angle RAO 30° CAU 30° that is determined as optimal for the intravascular intervention.

Thus, in the respective windows $W_{10}$ through $W_{14}$ on the monitor screen $20a$, the above-described third embodiment is adapted to display as synopsis the moving images of the three-dimensional image data $3D_{10}$, $3D_{11}$, $3D_{12}$, $3D_{13}$, $3D_{14}$ of the coronary artery 1a obtained by shifting the view angle, for instance, in the order of RAO 0 CRA 0→RAO 30° CRA 0 ... →RAO 30° CRA0 under the condition of being fixed for each of the cardiac phases 0%, 20%, 40%, 60%, 80% synchronously in terms of the view angle $F_j$ (j=10 through 17). The third embodiment provides advantages similar to those of the first embodiment.

Now, the fourth embodiment of the present invention will be described by referring to the related ones of the accompanying drawings. Note that the components same as those of FIG. 1 are denoted respectively by the same reference symbols.

Figure 16:
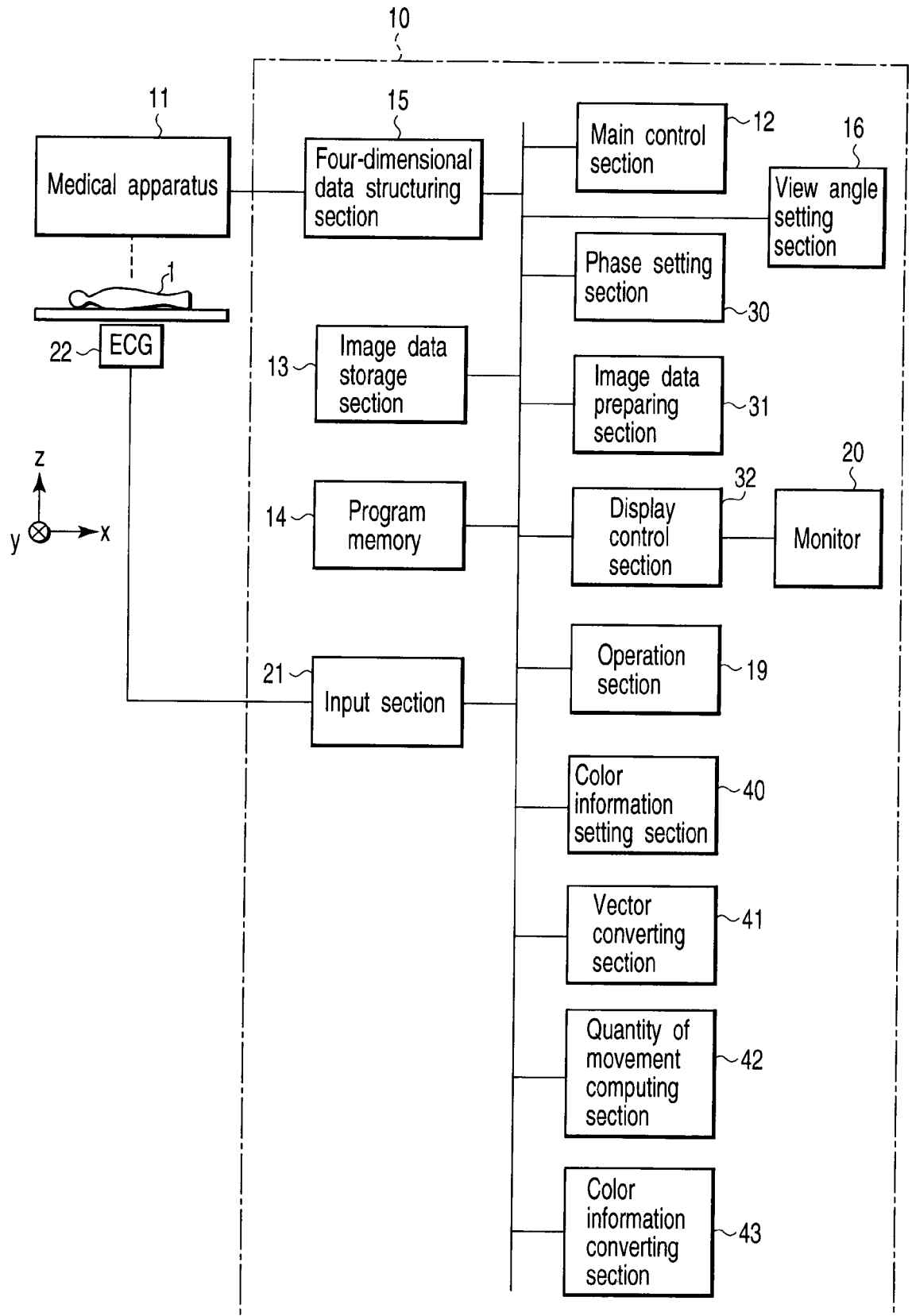
FIG. 16 is a schematic block diagram of a fourth embodiment of image display apparatus according to the present invention.

FIG. 16 is a schematic block diagram of the fourth embodiment of image display apparatus according to the present invention. Referring to FIG. 16, the image display apparatus main body 10 defines color information that corresponds to the quantity of the periodic contracting movement of the object of examination 1 and the quantity of movement of the coronary artery 1a that moves in response to the heartbeat and displays the color information that corresponds to the quantity of movement of the coronary artery 1a in the image of the coronary artery 1a displayed on the monitor screen 20a.

Figure 17:
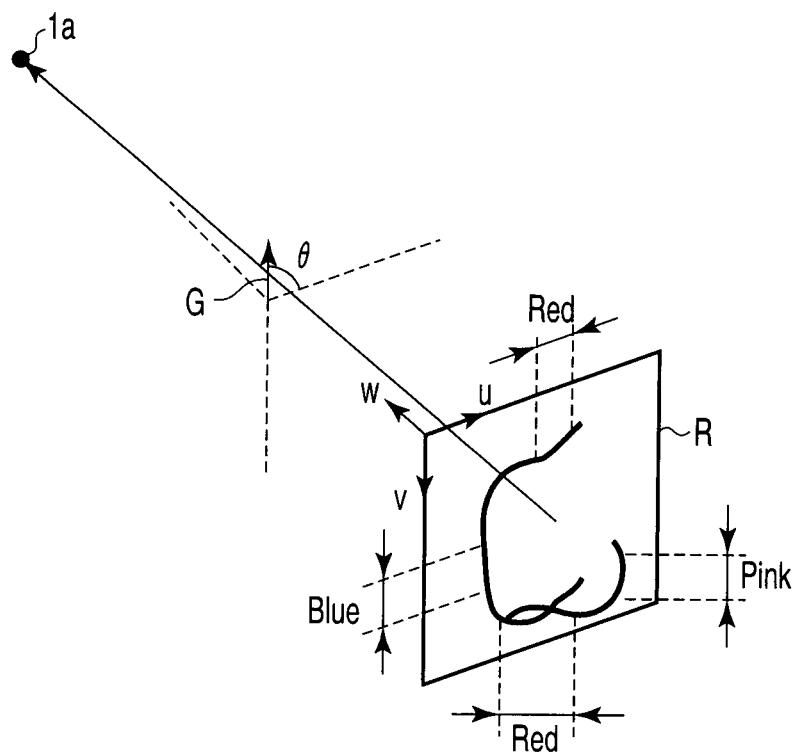
FIG. 17 is a schematic illustration of the operation of displaying color information corresponding to a quantity of movement of a coronary artery of the apparatus according to the fourth embodiment.
Figure 18:
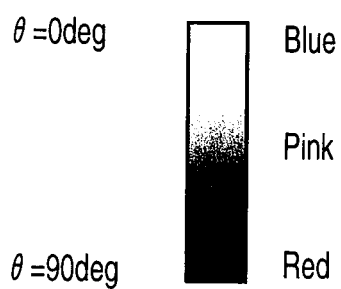
FIG. 18 is a schematic illustration of the relationship between angle θ and color information.

Two methods are provided to display color information. With the first method of displaying color information, the apparent quantity of movement of the coronary artery 1a running around the heart due to the heartbeat and hence the quantity of movement on the projection plane R in the u-v directions as shown in FIG. 17 is displayed in color. FIG. 17 illustrates that the quantity of movement of a spot on the coronary artery 1a due to the heartbeat is expressed typically by means of red, blue and pink. However, in reality, the quantity of movement of all the coronary artery 1a that is the total of the spots on the coronary artery 1a is expressed in color. If, for example, the apparent quantity of movement of the coronary artery 1a is greater than a first predetermined quantity of movement, the coronary artery 1a is displayed in red. If, to the contrary, the apparent quantity of movement of the coronary artery 1a is smaller than the first predetermined rate of movement, the coronary artery 1a is displayed in blue. Then, it will be clear that the use of angle θ that is close to the blue color is preferable. FIG. 18 illustrates the relationship between angle θ and color information.

Now, the apparent movement of the coronary artery 1 running around the heart due to the heartbeat will be described below in terms of the first color information display method by using three-dimensional image data 4D (x, y, z, t) as example. Assume that the image of the coronary artery 1a displayed on the monitor screen 20a is that of the coronary artery in a final stage of expansion of cardiac phase. Alternatively, the image of the coronary artery 1a displayed on the monitor screen 20a may be that of the coronary artery in a final stage of contraction of cardiac phase.

Figure 19:
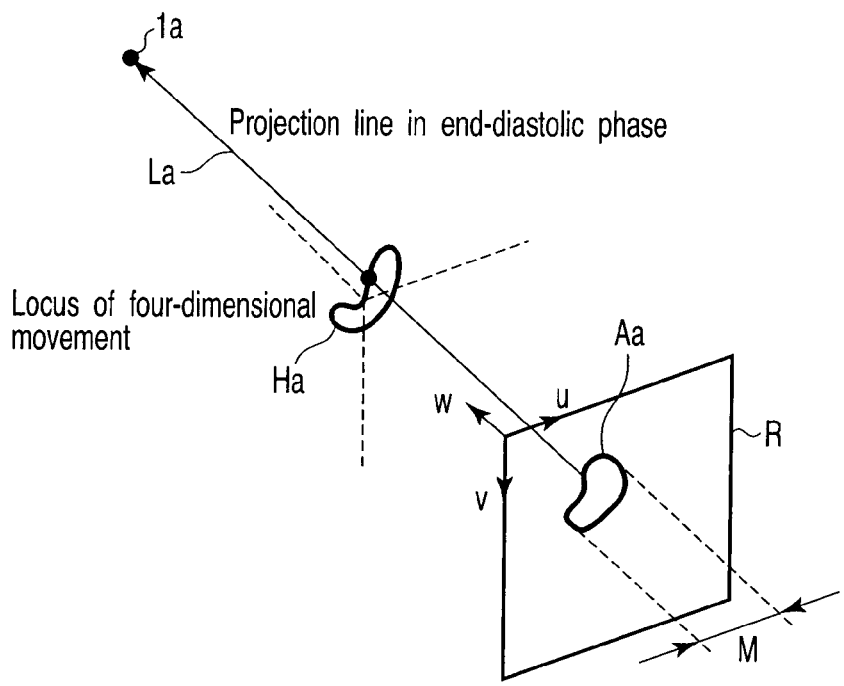
FIG. 19 is a schematic illustration of the apparent quantity of movement of a coronary artery due to the heartbeat that can be obtained by means of the first color information display method employed for the apparatus according to the fourth embodiment.

Referring to FIG. 19, the branching part of the coronary artery 1a moves with time in response to the heartbeat. Thus, when the branching part of the coronary artery 1a is projected onto the projection plane (u-v plane) R, it moves in the u-v directions on the projection plane R. La in FIG. 19 denotes the projection line on the projection plane R of the branching part of the coronary artery 1a in end-diastolic phase. Ha in FIG. 19 denotes the locus of movement of the coronary artery 1a on the projection line L1 in the four-dimensional space. As in FIG. 19 denotes the locus of movement of the coronary artery 1a on the projection plane R. Thus, the largest value (number of pixels) of amplitude in the projection plane R is defined as the apparent quantity of movement M of the coronary artery 1a in the projection plane R.

With the second color information display method, the changing rate of the foreshortening of the coronary artery 1a when the view angle is displaced from an optimal view angle, or the changing rate of the length of the vector G in the w-direction relative to the projection plane R as shown in FIG. 17, is displayed in color. If, for example, the changing rate of the length of the coronary artery 1a is greater than a predetermined second quantity of movement, the coronary artery 1a will be displayed in red. If, to the contrary, the changing rate of the length of the coronary artery 1a is smaller than the second predetermined rate of movement, the coronary artery 1a is displayed in blue. Then, it will be clear that the use of angle θ that is close to the blue color is preferable.

Figures 20A, 20B:
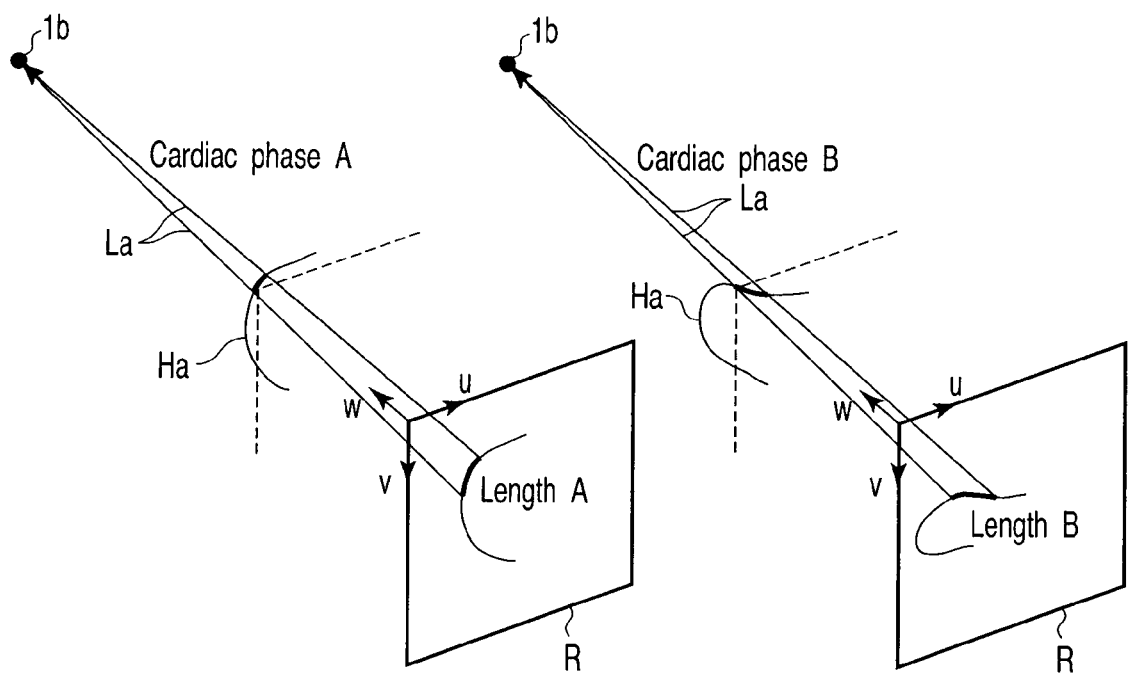
FIG. 20A is a schematic illustration of the rate of change of foreshortening of a coronary artery that can be obtained by means of the second color information display method employed for the fourth embodiment.
FIG. 20B is another schematic illustration of the rate of change of foreshortening of a coronary artery that can be obtained by means of the second color information display method employed for the fourth embodiment.

The changing rate of foreshortening of the coronary artery 1a will be described below for the second color information display method by using a stenotic part 1b of the coronary artery 1a in four-dimensional image data 4D (x, y, z, t) as an example, referring to FIGS. 20A and 20B. The stenotic part 1b of the coronary artery 1a is not changed by a heartbeat movement. On the other hand, the apparent stenotic length of the stenotic part 1b on the projection plane R is changed by a heartbeat movement. Thus, the changing rate of foreshortening is determined as the ratio of the length A in a cardiac phase where the length of the coronary artery 1a on the projection plane R appears longest to the length B in a cardiac phase where the length of the coronary artery 1a on the projection plane R appears shortest, or B/A. If the changing rate B/A of the coronary artery 1a is greater than the predetermined second quantity of movement, the stenotic part 1b is, for example, displayed in red. On the other hand, if the changing rate B/A of the coronary artery 1a is smaller than the predetermined second quantity of movement, the stenotic part 1b is, for example, displayed in blue.

The image display apparatus main body 10 includes a color information setting section 40, a vector conversion section 41, a quantity of movement computing section 42 and a color information converting section 43. The color information setting section 40, the vector conversion section 41, the quantity of movement computing section 42 and the color information converting section 43 operate according to the respective commands issued from the main control section 12.

The color information setting section 40 selects and sets a plurality of pieces of color information that correspond to the quantity of movement of the coronary artery 1a that varies as a function of the heartbeat. For example, red color is selected and set for the quantity of movement of the coronary artery 1a that is greater than a predetermined quantity of movement, whereas blue color is selected and set for the quantity of movement of the coronary artery 1a that is smaller than the predetermined quantity of movement.

Thus, with the first color information display method, for example, the coronary artery 1a is displayed in red when the apparent quantity of movement of the coronary artery 1a is greater than the first predetermined quantity of movement, whereas it is displayed in blue when the apparent quantity of movement of the coronary artery 1a is smaller than the first predetermined quantity of movement.

With the second color information display method, for example, the coronary artery 1a is displayed in red when the changing rate of the length of the coronary artery 1a is greater than the second predetermined quantity of movement, whereas it is displayed in blue when the changing rate of the length of the coronary artery 1a is smaller than the second predetermined quantity of movement. It should be noted, however, that color information selected and set by the color information setting section 40 is not limited to red and blue and a gray scale or a technique of changing the hatch density may alternatively be used.

The vector conversion section 41 converts the movement of the coronary artery 1a in a three-dimensional space due to the heartbeat movement into a three-dimensional movement vector G from the four-dimensional image data 4D (x, y, z, t) of the coronary artery 1a as shown in FIG. 17.

When the first color information display method is employed, the quantity of movement computing section 42 computationally determines the two-dimensional quantity of movement M in a two-dimensional plane of the coronary artery 1a, the two-dimensional plane being the projection plane R (u-v plane) where the three-dimensional movement vector G is projected. When the second color information display method is employed, the quantity of movement computing section 42 computationally determines the changing rate of the length of the vector G in the w-direction on the projection plane R.

If the first color information display method is employed, the color information converting section 43 converts the two-dimensional quantity of movement of the coronary artery 1a into color information that corresponds to the apparent quantity of movement M of the coronary artery 1a. If, on the other hand, the second color information display method is used, the color information converting section 43 converts the changing rate of the length of the coronary artery 1a into the color information that is selected and set by the color information setting section 40 and corresponds to the quantity of movement.

When the first color information display method is used, the display control section 18 displays the coronary artery 1a on the monitor screen 20a with the quantity of movement of the coronary artery 1a in the three-dimensional image data $3D_1$, $3D_2$, $3D_3$, . . . , $3D_9$ for the view angles $F_j$ (=$F_1$, $F_2$, $F_3$, . . . , $F_9$), or the color information that corresponds to the apparent quantity of movement M of the coronary artery 1a. When the second color information display method is used, the display control section 18 displays the coronary artery 1a on the monitor screen 20a with the changing rate of the length of the coronary artery 1a, or the color information that is selected and set by the color information setting section 40 and corresponds to the quantity of movement.

The program memory 14 stores the image display program to be executed by the main control section 12. The image display program is adapted to cause the image display apparatus to display a plurality of pieces of color information that correspond to the quantity of movement of the coronary artery 1a in the three-dimensional image data $3D_1$, $3D_2$, $3D_3$, . . . , $3D_9$ for the view angles $F_1$, $F_2$, $F_3$, . . . , $F_9$.

Now, the image display operation of the apparatus of the fourth embodiment having the above-described configuration will be described below by referring to the three-dimensional image data preparing flowchart of FIG. 21.

The medical equipment 11 images an object of examination 1 such as the coronary arteries 1a extending around and surrounding a heart showing a heartbeat movement and acquires image data on the object. The four-dimensional data structuring section 15 receives the image data on the object of examination acquired by the medical equipment 11 and structures four-dimensional image data (x, y, z, t) as shown in FIG. 2 from the image data.

On the other hand, the phase setting section 30 selects a plurality of cardiac phases that show a heartbeat movement, or the object of examination 1. The cardiac phases $i_k$ are selected from the electrocardiogram waveform acquired by means of an electrocardiograph 22 as shown in FIG. 32, for example, to the final stage of expansion of the heart and fixed to, for example, 0%, 20%, 40%, 60% and 80% such as in the third embodiment.

Then in Step #40, the image data preparing section 31 reads the cardiac phase $i_k$ that corresponds to a final stage of expansion of the heart set by the phase setting section 30. In Step #41, the image data preparing section 31 reads the four-dimensional image data 4D (x, y, z, t) stored in the image data storage section 13.

Then in Step #42, the image data preparing section 31 determines if it reads the four-dimensional image data 4D (x, y, z, t) of all the cardiac phases $i_k$ set by the phase setting section 30 or not. If it does not read the four-dimensional image data 4D (x, y, z, t) of all the cardiac phases $i_k$, it returns to Step #41 and repeats the operation until it reads the four-dimensional image data 4D (x, y, z, t) of all the cardiac phases $i_k$. Thus, as a result, the image data preparing section 31 prepares four-dimensional image data 4D (x, y, z, t) that correspond, for example, to the final stage of expansion of the heart.

Thereafter in Step #43, the vector conversion section 41 converts the movement of the coronary artery 1a in a three-dimensional space due to the heartbeat movement into a three-dimensional movement vector G from the four-dimensional image data 4D (x, y, z, t) of the coronary artery 1a as shown in FIG. 17.

Then in Step #44, the image data preparing section 31 reads view angles $F_j$ from the view angle setting section 16. The view angles $F_j$ may be, for example, $F_{j=10}$ (RAO 0, CRA 0), $F_{j=11}$ (RAO 30°, CRA 0), $F_{j=12}$ (RAO 30°, CAU 30), $F_{j=13}$ (RAO 0, CAU 30), $F_{j=14}$ (LAO 30°, CAU 30°), $F_{j=15}$ (LAO 30°, CRA 30°), $F_{j=16}$ (RAO 30°, CRA 30°), $F_{j=17}$ (RAO 30°, CRA 0°).

If the first color information display method is employed, the quantity of movement computing section 42 computationally determines the two-dimensional quantity of movement M of the coronary artery 1a in a two-dimensional plane on the projection plane R where the three-dimensional movement vector G is projected in Step #45, as shown in FIG. 19. If, on the other hand, the second color information display method is employed, the quantity of movement computing section 42 computationally determines the changing rate of the length of the vector G in the w-direction on the projection plane R as shown in FIGS. 20A and 20B.

Thereafter, when the first color information display method is selected, the color information converting section 43 converts the two-dimensional quantity of movement of the coronary artery 1a, or the apparent quantity of movement M of the coronary artery 1a, into the color information that is selected and set by the color information setting section 40 and corresponds to the quantity of movement. When, on the other hand, the second color information display method is selected, the color information converting section 43 converts the changing rate of the length of the coronary artery 1a into the color information that is selected and set by the color information setting section 40 and corresponds to the quantity of movement.

Then in Step #43, the image data preparing section 31 prepares three-dimensional image data (r, s, $i_k$) $3D_k$ of the movement of the coronary artery 1a projected onto the projection plane R when the view angle $F_j$ is shifted, for example, as RAO 0 CRA 0→RAO 30° CRA 0→RAO 30° CAU 30°→RAO 0 CAU 30°→LAO 30° CAU 30°→LAO 30° CRA 30°→RAO 30° CRA 30°→RAO 30° CRA 0 in a cardiac phase $i_k$ that corresponds to a final stage of expansion of the heart as in the case of the above described third embodiment.

Each of the three-dimensional image data $3D_k$ includes image data of a two-dimensional space (r, s) and temporal elements t ($=i_k$).

Figure 30:
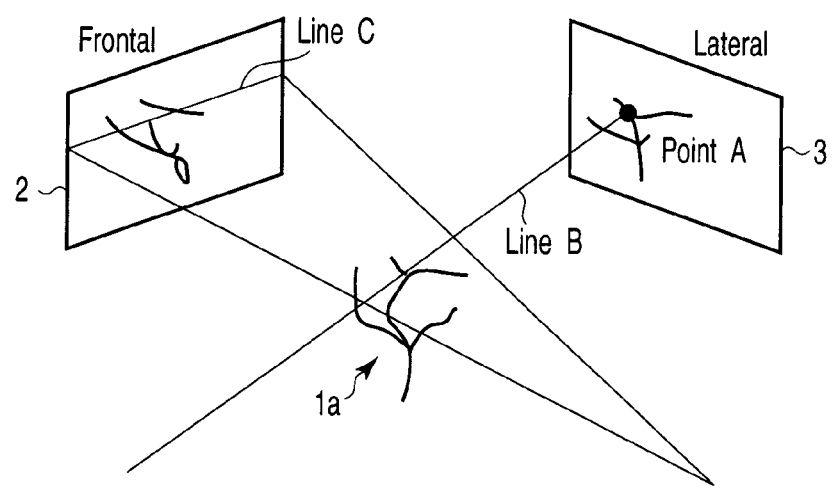
FIG. 30 is a schematic illustration of structuring a three-dimensional image by means of epipolar geometry.
Figure 31:
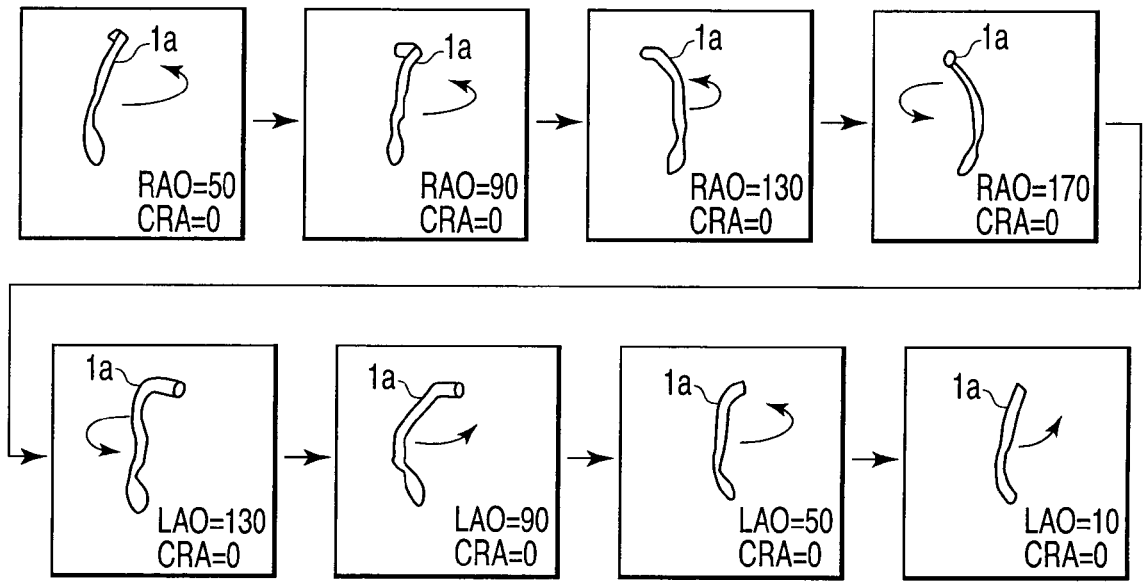
FIG. 31 is a schematic illustration of a rotating blood vessel being displayed on a monitor screen.

A technique of three-dimensionally displaying a blood vessel such as a coronary artery $1a$ (coronary 3D, coronary tree) from X-ray images in two directions as shown in FIG. 30 is employed when determining a optimal view angle for intravascular intervention. With the technique of three-dimensionally displaying a blood vessel, three-dimensional coordinates are computationally determined in the course of computations. When four-dimensional image data are computed for a plurality of cardiac phases, three-dimensional coordinates are computationally determined in the course of computations. Thus, with the technique of three-dimensionally displaying a blood vessel, it is possible to determine four-dimensional coordinates and hence the locus Ha of movement of a coronary artery $1a$ on projection line La in a four-dimensional space as shown in FIG. 19.

With the technique of three-dimensionally displaying a blood vessel, the position of a coronary artery $1a$ in a three-dimensional space is determined as the surgeon who is going to perform an intravascular intervention manually points it on Frontal image 2 as shown in FIG. 30. In other words, it is necessary to specify the coordinates of a point on Frontal image 2 and those of the corresponding point on Lateral image 3. With this arrangement, it is possible to find out the three-dimensional coordinates of a stenotic part of a coronary artery $1a$ as the surgeon who is going to perform an intravascular intervention points the stenotic part of the coronary artery $1a$ as corresponding point. Generally, the surgeon points a plurality of corresponding points (characteristic points) on coronary artery $1a$. The number will typically be about 3 to 10. Then, corresponding points are linearly selected between those characteristic points. As a result, it is possible to find out the three-dimensional coordinates of all the points on the coronary artery $1a$ by means of the characteristic points and the corresponding points.

The medical equipment 11 may typically be an X-ray apparatus, an X-ray CT apparatus, an MRI apparatus, a PET apparatus, a SPECT apparatus, a US apparatus, an IVUS apparatus or an X-ray diagnostic apparatus. However, unlike the technique of three-dimensionally displaying a blood vessel, it is not possible to acquire coordinate information from the data restructured by an X-ray CT apparatus or an MRI apparatus. If such is the case, characteristic points are selected on three-dimensional image data and points that resemble such characteristic points are searched for on the corresponding four-dimensional image data to determine the locus of movement in a four-dimensional space.

The image data preparing section 31 receives the apparent quantity of movement M of the coronary artery $1a$ when the first color information display method is used or the changing rate of the length of the coronary artery $1a$ when the first color information display method from the color information converting section 43 is employed. Then, the image data preparing section 31 adds color information to the three-dimensional image data (r, s, $i_k$) $3D_k$. The position on the three-dimensional image data (r, s, $i_k$) $3D_k$ where color information is added is the position of the coordinates of the coronary artery $1a$ that corresponds to the quantity of movement M of the coronary artery $1a$ or the changing rate of the length of the coronary artery $1a$.

Then in Step #44, the image data preparing section 31 sends the three-dimensional image data (r, s, $i_k$) $3D_k$ and the color information that show, for instance, the movement of the coronary artery $1a$ in the cardiac phase $i_k$ corresponding to a final stage of expansion of the heart to the display control section 18.

Figure 22:
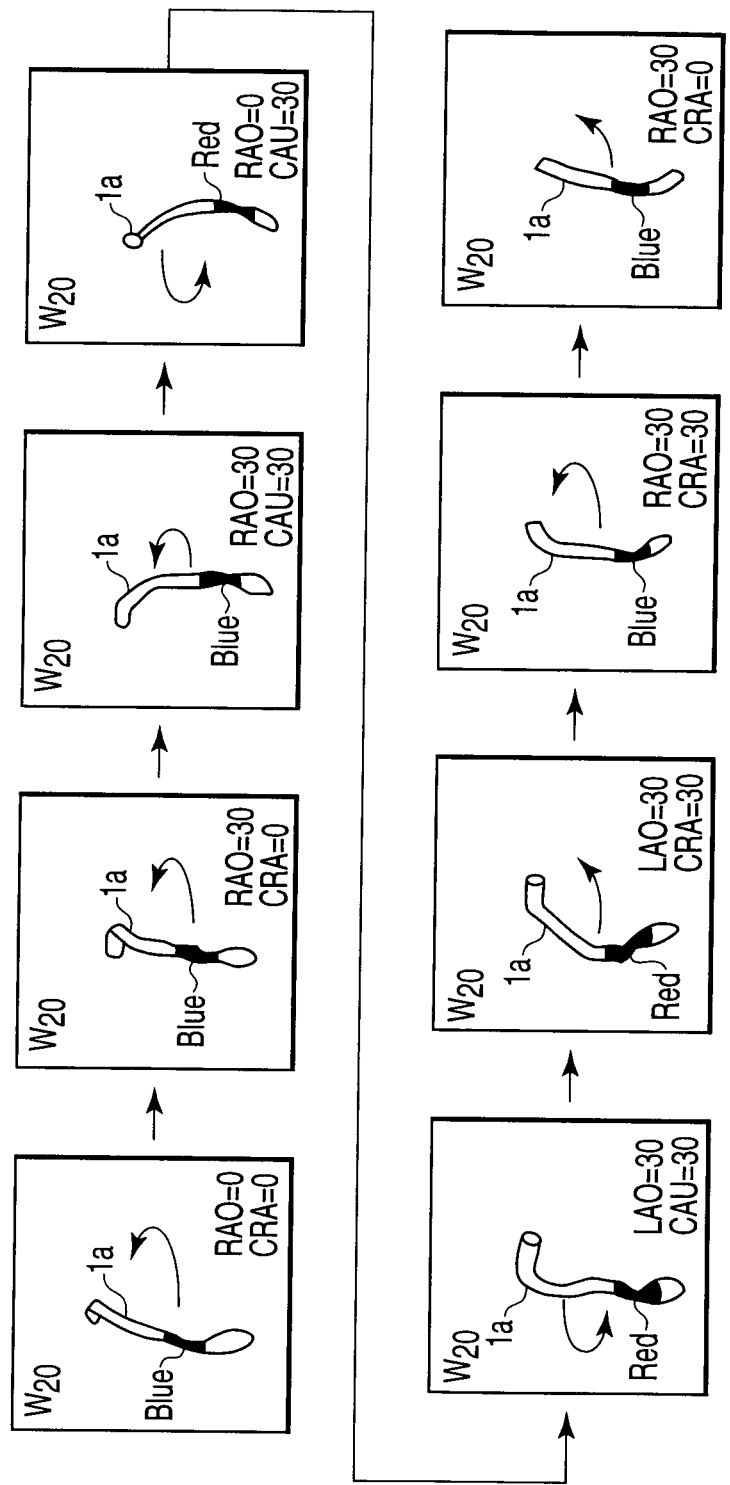
FIG. 22 is a schematic illustration of an exemplary display of the quantity of movement of a coronary artery, using color information, while moving the view angle relative to the coronary artery of the apparatus according to the fourth embodiment.

Then, the display control section 18 displays a window $W_{20}$ typically as shown in FIG. 22 on the monitor screen $20a$ of the monitor 20. Thus, the display control section 18 displays a moving image of the heart from view angle $F_j$ that typically shifts as RAO 0 CRA 0→RAO 30° CRA 0→RAO 30° CAU 30°→RAO 0 CAU 30°→LAO 30° CAU 30°→LAO 30° CRA 30°→RAO 30° CRA 30°→RAO 30° CRA 0 in a cardiac phase $i_k$ that corresponds to a final stage of expansion of the heart. At this time, the color of the coronary artery $1a$ displayed on the monitor screen $20a$ changes according to the apparent quantity of movement M of the coronary artery $1a$ when the first color information display method is used or the changing rate of the length of the coronary artery $1a$ when the second color information display method is used.

With the first color information display method, the coronary artery $1a$ is displayed in red when the apparent quantity of movement M of the coronary artery $1a$ is greater than a predetermined first quantity of movement, whereas it is displayed in blue when the apparent quantity of movement M of the coronary artery $1a$ is smaller than the predetermined first quantity of movement.

With the second color information display method, on the other hand, the coronary artery $1a$ is displayed in red when the changing rate of the length of the coronary artery $1a$ is greater than a predetermined second quantity of movement, whereas it is displayed in blue when the changing rate of the length of the coronary artery $1a$ is smaller than the predetermined second quantity of movement.

Figure 21:
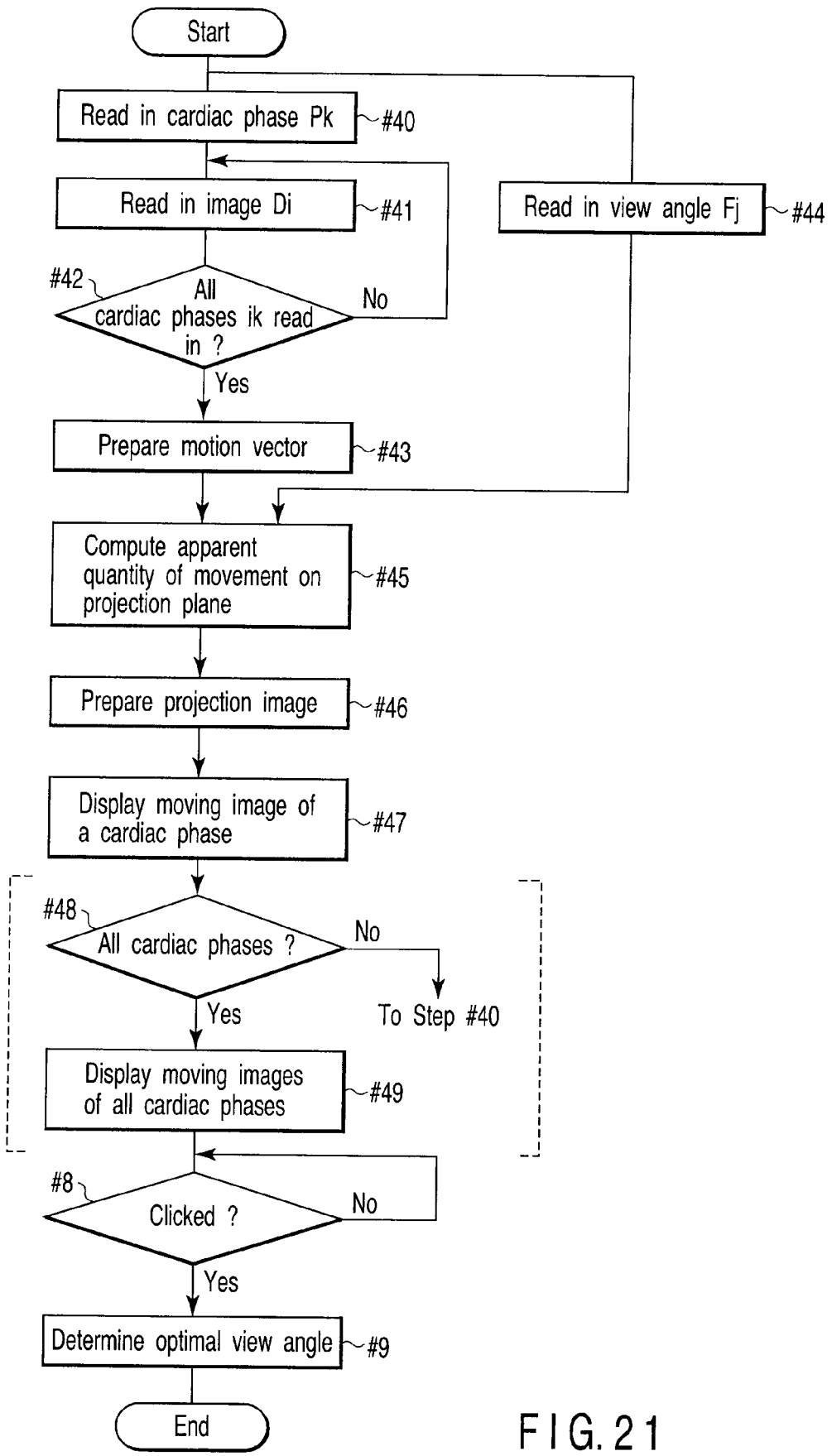
FIG. 21 is a flowchart of the process of preparing three-dimensional image data of the apparatus according to the fourth embodiment.

Note that, while the coronary artery $1a$ is displayed partly in red or blue for the sake of convenience of illustration in FIG. 21, the apparent quantity of movement M or the changing rate of the length of the coronary artery $1a$ varies from part to part in reality. Therefore, the display color of the coronary artery $1a$ may vary from part to part depending on the apparent quantity of movement M or the changing rate of the length of each part of the coronary artery $1a$. Thus, the each part of the coronary artery $1a$ may be displayed in red, yellow, blue, green, brown or some other color depending on the apparent quantity of movement M or the changing rate of the length of the part.

Then in Step #8, the display control section 32 determines which view angle $F_j$ is selected by clicking the mouse of the operation section 19. The surgeon who is going to perform an intravascular intervention operates the mouse of the operation section 19. In response to the operation, a pointer P is arranged on the window $W_{20}$ on the monitor screen $20a$. The display control section 18 receives the click operation. Then in Step #9, the display control section 18 determines, for example, the view angle $F_j$ at the time when the pointer P is clicked in the moving image in the window $W_{20}$, which may be RAO 30° CAU 30° for example, as optimal view angle.

Thereafter, the main control section 12 stores the view angle RAO 30° CAU 30° that is determined as optimal view angle in a memory such as RAM and also transmits it to the medical equipment 11. The medical equipment 11 drives the C arm to rotate in the above described manner in order to move the X-ray source and the X-ray detector to respective positions that correspond to the view angle RAO 30° CAU 30°. As a result, it is possible to acquire a moving image of the coronary artery $1a$ produced by imaging the coronary artery $1a$ from the view angle RAO 30° CAU 30° that is determined as optimal for the intravascular intervention.

After the operation in Step #47, the image data preparing section 31 may move to Steps #48, #49 to display the moving images of the coronary artery al in all the cardiac phases $i_k$ as synopsis. More specifically in Step #48, the image data preparing section 31 determines if it acquires the three-dimensional image data (r, s, $i_k$) $3D_k$ and the color information showing the movement of the coronary artery 1a in cardiac phases of 0%, 20%, 40%, 60% and 80% in addition to the three-dimensional image data in the cardiac phase that corresponds to end-diastolic phase.

If the image data preparing section 31 determines that it does not acquire the three-dimensional image data (r, s, $i_k$) $3D_k$ and the color information in all the cardiac phases $i_k$, it returns to Step #30. If, on the other hand, the image data preparing section 31 determines that it acquires the three-dimensional image data (r, s, $i_k$) $3D_k$ and the color information in all the cardiac phases $i_k$, it moves to Step #46, where it displays a plurality of windows including the window $W_{20}$ that correspond to all the cardiac phases $i_k$ on the monitor screen 20a. Then, the image data preparing section 31 displays the moving images of the three-dimensional image data (r, s, $i_k$) $3D_k$ and the color information in all the cardiac phases in the respective windows.

Thus, the above-described fourth embodiment selects and sets a plurality of pieces of color information for indicating the quantity of movement of the coronary artery 1a that corresponds to the heartbeat and displays the color information that corresponds to the quantity of movement of the coronary artery 1a, while shifting the view angle $F_j$ relative to the coronary artery 1a in the image of the coronary artery 1a that is being displayed on the monitor screen 20a. With this arrangement, it is possible to see the movement of the coronary artery 1a when the heart beats by way of the color information of red color and/or blue color, for instance, while shifting the view angle $F_j$ relative to the coronary artery 1a.

The coronary artery 1a can be displayed not only in the cardiac phase corresponding to a final stage of expansion of the heart but also in cardiac phases of 0%, 20%, 40%, 60% and 80%, while shifting the view angle $F_j$ relative to the coronary artery 1a. Then, it is possible to see the movement of the coronary artery 1a by way of the color information of red color and/or blue color, for instance. Thus, it is possible to see the overall movement of the coronary artery 1a simply by seeing the displayed image of the coronary artery 1a.

While a plurality of pieces of color information are selected and set so as to correspond to different quantities of movement of the coronary artery 1a that takes place in response to a heartbeat in the above described fourth embodiment, pieces of color information may be so selected and set as to correspond to moving directions (x, y, z) of the coronary artery 1a.

Now, the fifth embodiment of the present invention will be described below by referring to the related ones of the accompanying drawings. Note that the components same as those of FIGS. 1 and 10 are denoted respectively by the same reference symbols and will not be described any further.

Figure 23:
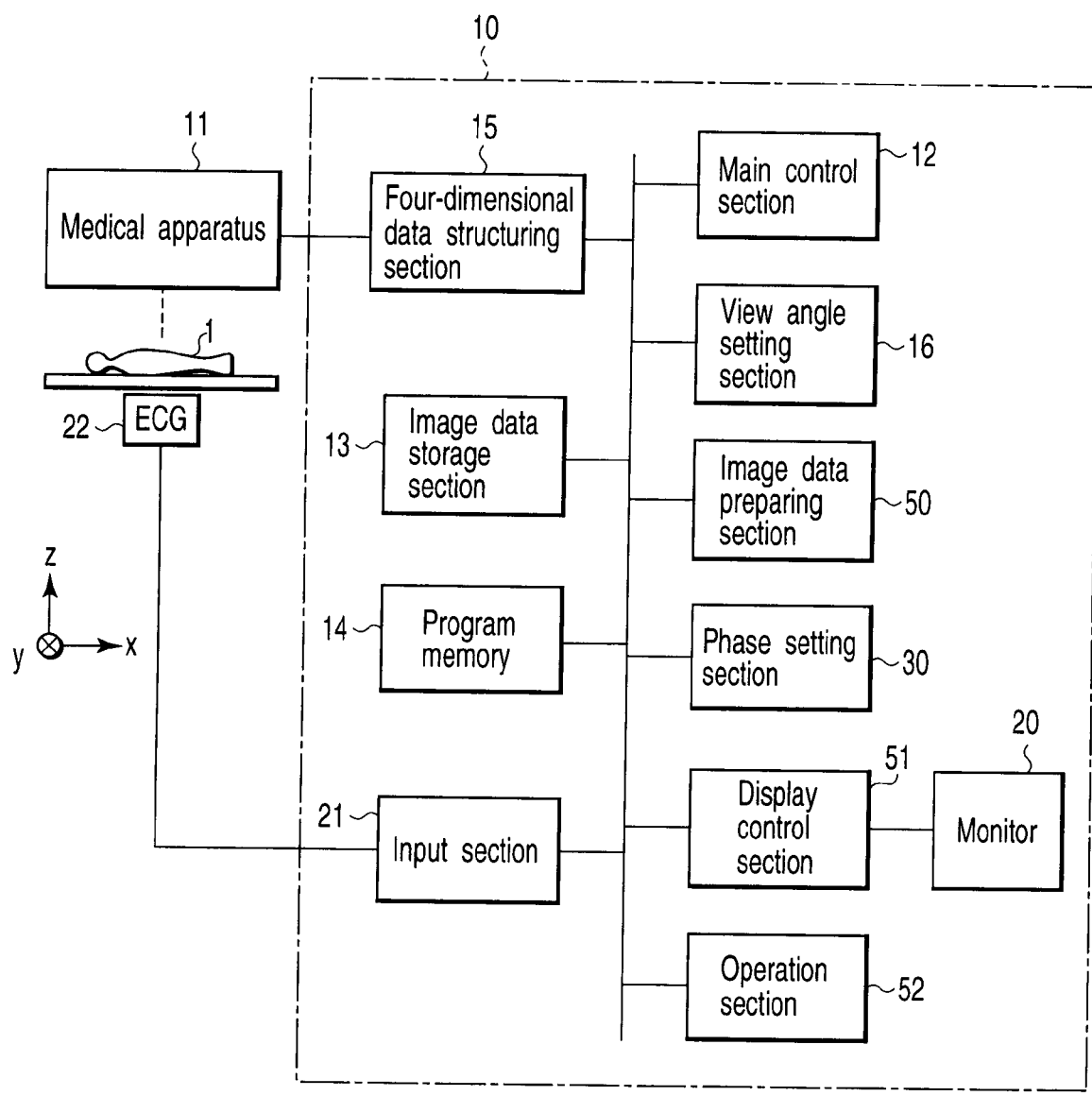
FIG. 23 is a schematic block diagram of a fifth embodiment of image display apparatus according to the present invention.

FIG. 23 is a schematic block diagram of the image display apparatus of this embodiment. The image display apparatus main body 10 includes an image data preparing section 50 and a display control section 51. The image data preparing section 50 and the display control section 51 operate according to the respective commands issued from the main control section 12.

The operation section 52 typically includes a mouse. Each time the mouse is clicked, the operation section 52 switches the image data prepared by the image data preparing section 50, which are the three-dimensional image data (u, v, t) for forming a moving image of the coronary artery 1a that moves in response to the heartbeat under the condition that the view angle $F_j$ is fixed and set to the three-dimensional image data (r, s, t) for forming a moving image of the coronary artery 1a that is observed when the view angle $F_j$ is shifted relative to the coronary artery 1a under the condition that the heartbeat movement is fixed and vice versa and outputs a switching operation signal for displaying the moving images in a switched manner.

Each time the image data preparing section 50 receives a switching operation signal output from the operation section 52, it prepares the first three-dimensional image data (u, v, t) for forming an moving image of the coronary artery 1a that moves in response to the heartbeat under the condition that the view angle $F_j$ is fixed and set from the four-dimensional image data 4D (x, y, z, t). Additionally, each time the image data preparing section 50 receives a switching operation signal output from the operation section 52, it prepares the second three-dimensional image data (r, s, t) for forming a moving image of the coronary artery 1a that is produced by shifting the view angle $F_j$ relative to the coronary artery 1a under the condition that the heartbeat is fixed from the four-dimensional image data 4D (x, y, z, t).

Each time the display control section 51 receives a switching operation signal output from the operation section 52, it displays the moving image of the first three-dimensional image data (u, v, t) or the moving image of the second three-dimensional image data (r, s, t) prepared by the image data preparing section 50 in a switched manner.

The program memory 14 stores the image data program to be executed by the main control section 12. Each time the image display program receives a switching operation signal output from the operation section 52, it causes the image data apparatus to display the moving image of the first three-dimensional image data (u, v, t) showing the coronary artery 1a that moves in response to the heartbeat under the condition that the view angle $F_j$ is fixed and set or the moving image of the second three-dimensional image data (r, s, t) produced by shifting the view angle $F_j$ relative to the coronary artery 1a under the condition that the heartbeat is fixed in a switched manner.

Figure 24:
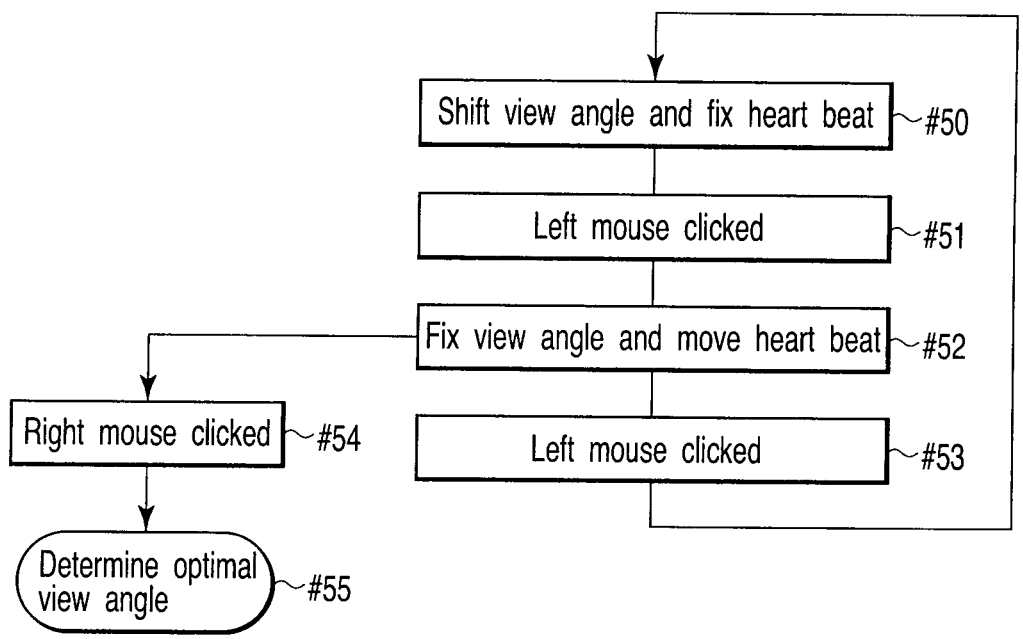
FIG. 24 is a flowchart of the process of preparing three-dimensional image data of the apparatus according to the fifth embodiment.

Now, the operation of the apparatus of the fifth embodiment of the present invention will be described below by referring to the three-dimensional image data preparing flowchart of FIG. 24.

The medical equipment 11 images an object of examination 1 such as the coronary arteries 1a extending around and surrounding a heart showing a heartbeat movement and acquires image data on the object. The four-dimensional data structuring section 15 receives the image data on the object of examination 1 acquired by the medical equipment 11 and structures four-dimensional image data (x, y, z, t) as shown in FIG. 2 from the image data.

Each time the image data preparing section 50 receives a switching operation signal output from the operation section 52, it prepares the first three-dimensional image data (u, v, t) for forming a moving image of the coronary artery 1a that moves in response to the heartbeat under the condition that the view angle $F_j$ is fixed and set from the four-dimensional image data 4D (x, y, z, t).

Additionally, each time the image data preparing section 50 receives a switching operation signal output from the operation section 52, it prepares the second three-dimensional image data (r, s, t) for forming a moving image of the coronary artery 1a produced by shifting the view angle $F_j$ relative to the coronary artery 1a under the condition where the heartbeat is fixed from the four-dimensional image data 4D (x, y, z, t).

More specifically, in Step #50, the image data preparing section 50 prepares the second three-dimensional image data (r, s, t) for forming a moving image of the coronary artery 1a produced by shifting the view angle $F_j$ relative to the coronary artery 1a under the condition that the heartbeat is fixed and hence the cardiac phase is fixed. The display control section 51 then displays the moving image of the second three-dimensional image data (r, s, t) obtained by shifting the view angle $F_j$ under the condition that the heartbeat is fixed as indicated by display condition $Q_1$ in FIG. 25 on the monitor screen 20a.

Figure 26:
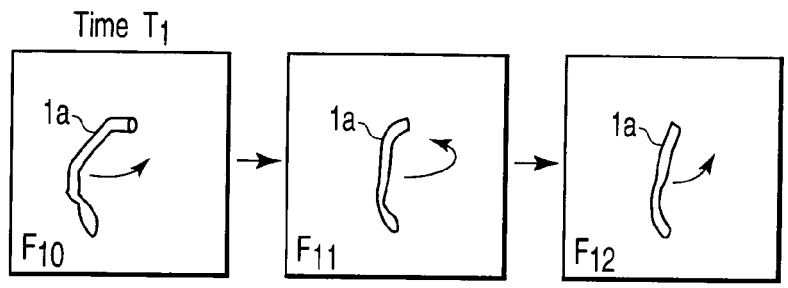
FIG. 26 is a schematic illustration of a moving image that can be displayed on the apparatus of the fifth embodiment by moving the view angle relative to a coronary artery under the condition that a cardiac phase is fixed.

FIG. 26 schematically illustrates a moving image of the second three-dimensional image data (r, s, t) produced by shifting the view angle $F_j$ relative to the coronary artery 1a under the condition that the cardiac phase $i_k$ is fixed. In FIG. 26, the arrows indicate that the coronary artery 1a rotates when the view angle $F_j$ is shifted successively from $F_{10}$ to $F_{11}$ and $F_{12}$.

As the surgeon who is going to perform an intravascular intervention clicks the mouse of the operation section 52 under this condition, the operation section 52 outputs a switching operation signal for switching the image being displayed on the monitor screen 20a in Step #51.

As the image data preparing section 50 receives the switching operation signal output from the operation section 52 in Step #52, it switches from preparation of the second three-dimensional image data (r, s, t) for the moving image of the coronary artery 1a produced by shifting the view angle $F_j$ relative to the coronary artery 1a under the condition that the cardiac phase $i_k$ is fixed to preparation of the first three-dimensional image data (u, v, t) for the moving image of the coronary artery 1a moving in response to the heartbeat under the condition that the view angle $F_j$ is fixed and set.

If the click operation is conducted at time $T_1$ as shown in FIG. 26 and the view angle $F_j$ of the second three-dimensional image data (r, s, t) is $F_{10}$ at that time, the image data preparing section 50 prepares the first three-dimensional image data (u, v, t) for the moving image of the coronary artery 1a moving in response to the heartbeat under the condition that the view angle $F_{10}$ is fixed and set.

Figure 25:
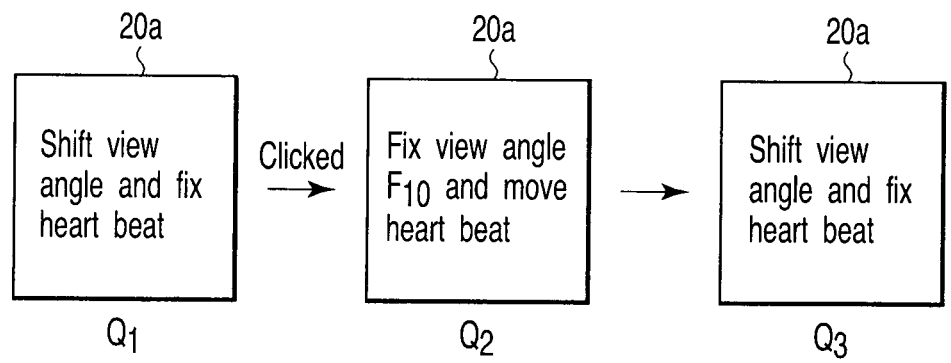
FIG. 25 is a schematic illustration of switching an image that can be displayed of the apparatus according to the fifth embodiment.
Figure 27:
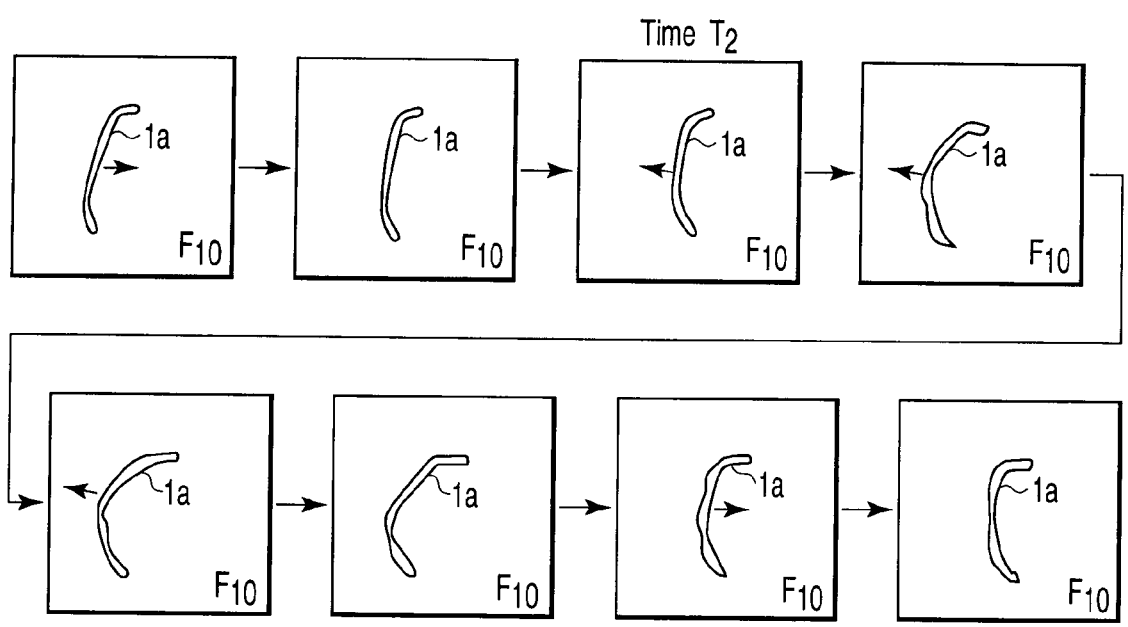
FIG. 27 is a schematic illustration of a moving image of a coronary artery of a heart moving according to the heartbeat thereof that can be displayed on the apparatus of the fifth embodiment under the condition that a cardiac phase is fixed.

Then, the display control section 51 displays the moving image of the first three-dimensional image data (u, v, t) prepared by the image data preparing section 50 on the monitor screen 20a under the display condition as illustrated in $Q_2$ in FIG. 25. The moving image of the first three-dimensional image data (u, v, t) may be that of the coronary artery 1a moving in response to the heartbeat under the condition that the view angle $F_{10}$ is fixed and set as shown in FIG. 27. The arrows in the windows in FIG. 27 indicate the directions in which the coronary artery 1a moves.

As the surgeon who is going to perform an intravascular intervention clicks the mouse of the operation section 52 once again under this condition, the operation section 52 outputs a switching operation signal for the image being displayed on the monitor screen 20a in Step #53. Assume that the click operation is performed at time $T_2$ and the moving image of the second three-dimensional image data (r, s, t) obtained from the view angle $F_{10}$ is being displayed on the monitor screen 20a.

Then, the image data preparing section 50 returns to Step #50, where it prepares the second three-dimensional image data (r, s, t) of the moving image obtained when the view angle $F_j$ relative to the coronary artery 1a is shifted successively from $F_{10}$ to $F_{11}$ and $F_{12}$ under the condition that the cardiac phase $i_k$ is fixed. Then, the display control section 51 displays the moving image of the second three-dimensional image data (r, s, t) produced by successively shifting the view angle $F_j$ from $F_{10}$ to $F_{11}$ and $F_{12}$ under the condition that the heartbeat movement is fixed as indicated by the display condition $Q_3$ in FIG. 25 on the monitor screen 20a.

Thereafter, each time the mouse is clicked, the moving image of the first three-dimensional image data (u, v, t) of the coronary artery 1a moving in response to the heartbeat under the condition that the view angle $F_j$ is fixed is switched to the moving image of the second three-dimensional image data (r, s, t) of the coronary artery 1a produced by shifting the view angle relative to the coronary artery 1a under the condition that the cardiac phase $i_k$ is fixed or vice versa.

If the surgeon who is going to perform an intravascular intervention makes right mouse click while the moving image of the first three-dimensional image data (u, v, t) of the coronary artery 1a moving in response to the heartbeat under the condition that the view angle $F_j$ is fixed to $F_{10}$ as shown in FIG. 27, the display control section 51 determines that the view angle $F_{10}$ of the first three-dimensional image data (u, v, t) of the moving image being displayed on the monitor screen 20a is an optimal view angle in Step #55.

Thus, the fifth embodiment displays the moving image of the first three-dimensional image data (u, v, t) of the coronary artery 1a moving in response to the heartbeat under the condition that the view angle $F_j$ is fixed or the moving image of the second three-dimensional image data (r, s, t) of the coronary artery 1a produced by shifting the view angle $F_j$ relative to the coronary artery 1a under the condition that the cardiac phase $i_k$ is fixed in a switched manner each time the mouse is clicked. Then, it is possible to determine an optimal view angle for an intravascular intervention from the moving image of the coronary artery 1a moving in response to the heartbeat under the condition that the view angle $F_j$ is fixed and the moving image of the coronary artery 1a produced by shifting the view angle $F_j$ relative to the coronary artery 1a under the condition that the heartbeat movement is fixed.

While the above-described fifth embodiment switches the display of the moving image of the three-dimensional image data (u, v, t) to that of the moving image of the three-dimensional image data (r, s, t) or vice versa by way of a click operation of the mouse, the present invention is by no means limited thereto. It may alternatively be so arranged that the coronary artery 1a is displayed while the view angle $F_j$ is being shifted when the mouse is pushed down but the coronary artery 1a that is moving in response to the heartbeat is displayed while the view angle $F_j$ is fixed when the mouse is not pushed down.

Still alternatively, it may be so arranged that the coronary artery 1a that is moving in response to the heartbeat is displayed while the view angle $F_j$ is fixed when the mouse is pushed down but the coronary artery 1a is displayed while the view angle $F_j$ is being shifted when the mouse is not pushed down. Still alternatively, it may be so arranged that the coronary artery 1a is displayed while the view angle $F_j$ is being shifted when the mouse is left-clicked but the coronary artery 1a that is moving in response to the heartbeat is displayed while the view angle $F_j$ is fixed when the mouse is right-clicked and either the moving image of the three-dimensional image data (u, v, t) or that of the three-dimensional image data (r, s, t), whichever appropriate, is made still when the mouse is not clicked at either side.

A joystick may alternatively be used. It may be so arranged that the view angle $F_j$ is shifted in response to an operation of shifting the angle of tilting the joystick when displaying the coronary artery 1a and the view angle $F_j$ is fixed to display the coronary artery 1a moving in response to the heartbeat in response to a button operation. With this arrangement, it is possible to determine the view angle by the direction in which the joystick is tilted.

For switching from the three-dimensional image data (u, v, t) to the three-dimensional image data (r, s, t) or vice versa, it may be so arranged that the operation of displaying the coronary artery 1a, shifting the view angle $F_j$, is terminated when the view angle $F_j$ is turned by 360° and switched to the operation of displaying the coronary artery 1a moving in response to the heartbeat under the condition that the view angle $F_j$ is fixed. It may alternatively be so arranged that the operation of displaying the coronary artery 1a moving in response to the heartbeat under the condition that the view angle $F_j$ is fixed is terminated when a heartbeat is completed and switched to the operation of displaying the coronary artery 1a, shifting the view angle $F_j$.

With the technique of three-dimensionally displaying a blood vessel such as a coronary artery 1a from X-ray images taken from two directions, it is difficult to see the detailed structure of the coronary artery 1a due to the phenomenon of foreshortening where the apparent length of the coronary artery 1a is shortened. Therefore, according to the present invention, a moving image of the coronary artery 1a acquired by angiography is displayed on the monitor screen 20a. Then, one or more moving images acquired by one of the first through fifth embodiments are displayed synchronously with the display of the moving image of the coronary artery 1a.

For example, when the first embodiment is applied, moving images of a plurality of three-dimensional image data (u, v, t) 3D showing how the coronary artery 1a moves in response to the heartbeat under the condition that the plurality of view angles $F_1$ through $F_j$ are fixed are displayed synchronously with the moving image of the coronary artery 1a acquired by angiography.

With such a display technique, it is possible to observe the detailed structure of the coronary artery 1a from the moving image acquired by angiography. At the same time, it is possible to recognize the phenomenon of foreshortening where the apparent length of the coronary artery 1a is shortened from the display of one or more moving images by means of one of the first through fifth embodiments.

The above described fourth embodiment displays color information that corresponds to the quantity of movement of the coronary artery 1a, while shifting the view angle relative to the coronary artery 1a. However, the present invention is by no means limited thereto and the first through third and the fifth embodiments may be adapted to display color information corresponding to the quantity of movement of the coronary artery 1a on the image of the coronary artery 1a being displayed on the monitor screen 20a.

The above-described first through fifth embodiments are adapted to view a coronary artery 1a. However, the present invention is by no means limited thereto and they may be so adapted as to display the entire heart to determine an optimal view angle for a surgery operation. They may alternatively be so adapted to display an organ other than the heart to determine an optimal view angle for a surgery operation without being influenced by any movement attributable to breathing.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An image display method which displays an image of an object of examination showing a periodic contracting movement by image processing performed by a computer, the image display method comprising:
    defining a plurality of view angles, wherein each of the view angles with respect to the object of examination is less than 90 degrees, and defining at least three kinds of phases in the contracting movement of the object of examination, each view angle comprising a combination of a first angle expressed in terms of a head direction and a tail direction and a second angle including a first oblique direction and a second oblique direction with respect to the object of the examination;
    preparing a plurality of first three-dimensional image data including temporal elements according to the view angles from four-dimensional data including the temporal elements of the object of examination, or a plurality of second three-dimensional image data including the temporal elements in which each of the view angles for the object of examination has been moved at one of the first angle and the second angle combinations with respect to the object of examination for each of the phases, from the four-dimensional image data, with each phase fixed;
    movie displaying, on a monitor screen, the plurality of first three-dimensional image data of the object of examination showing the contracting movement as respective moving images at the same time under the condition of fixing each of the view angles, the moving images being arranged in vertical and horizontal directions of the monitor screen, or movie displaying, on the monitor screen, the plurality of second three-dimensional image data as respective moving images at the same time under the condition of fixing the phase, after the plurality of second three-dimensional image data has been moved at one of the first angle and the second angle combinations; and
    determining, after one of the plurality of first three-dimensional image data displayed as the respective moving images at the same time on the monitor screen is selected or one of the plurality of second three-dimensional image data displayed as the respective moving images at the same time on the monitor is selected, a first view angle or a second view angle, which is associated with the selected one of the plurality of first three-dimensional image data or the selected one of the plurality of second three-dimensional image data, as an optimal view angle.

2. The image display method according to claim 1, wherein the first three-dimensional image data are displayed on the monitor screen simultaneously as a synopsis, synchronizing the temporal elements.

3. The image display method according to claim 1, wherein
    a plurality of pieces of color information are defined to correspond to a quantity of the periodic contracting movement of the object of examination; and
    the color information is displayed in the first three-dimensional image data of the object of examination.

4. The image display method according to claim 1, wherein
    a first moving image is prepared for an arbitrarily selected one of the view angles from the four-dimensional image data;
    a second moving image is prepared by shifting the view angle relative to the object over the plurality of view angles from the four-dimensional image data under the condition that the contracting movement of the object of examination is fixed; and the first moving image and the second moving image are displayed alternatively on the monitor screen in response to input by an operator.

5. An image display apparatus, comprising:

a view angle defining section configured to define a plurality of view angles, wherein each of the view angles with respect to an object of examination showing a periodic contracting movement is less than 90 degrees, each view angle comprising a combination of a first angle expressed in terms of a head direction and a tail direction and a second angle including a first oblique direction and a second oblique direction with respect to the object of the examination;

a phase setting section configured to set at least three kinds of phases in the contracting movement of the object of examination;

a monitor having a monitor screen;

an image data preparing section configured to prepare a plurality of first three-dimensional image data including the temporal elements of the view angles from four-dimensional image data on the object of examination including the temporal elements, or a plurality of second three-dimensional image data including the temporal elements in which each of the view angles for the object of examination has been moved at one of the first angle and the second angle combinations with respect to the object of examination for each of the phases, from the four-dimensional image, with each phase fixed; and a display control section configured to movie display the plurality of first three-dimensional image of the object of examination showing the contracting movement on the monitor screen as respective moving images at the same time under the condition of fixing the plurality of view angles, the moving images being arranged in vertical and horizontal directions of the monitor screen, or movie displaying, on the monitor screen, the plurality of second three-dimensional image data as respective moving images at the same time under the condition of fixing the phase, after the plurality of second three-dimensional image data has been moved at one of the first angle and the second angle combinations, and configured to determine, after one of the plurality of first three-dimensional image data displayed as the respective moving images at the same time on the monitor screen is selected or one of the plurality of second three-dimensional image data displayed as the respective moving images at the same time on the monitor is selected, a first view angle or a second view angle, which is associated with the selected one of the plurality of first three-dimensional image data or the selected one of the plurality of second three-dimensional image data, as an optimal view angle.

6. The image display apparatus according to claim 5, wherein the display control section displays the first three-dimensional image data on the monitor screen simultaneously as a synopsis, synchronizing the temporal elements.

7. An image display apparatus, comprising: a phase defining section configured to define a plurality of phases of a contracting movement of an object of examination showing a periodic contracting movement, the plurality of phases including at least three kinds of phases;

a monitor having a monitor screen;

an image data preparing section configured to prepare a plurality of three-dimensional image data, including temporal elements in which each viewing angle of a plurality of view angles for the object of examination has been moved for each of the phases, from four-dimensional image data, each view angle comprising a combination of a first angle expressed in terms of a head direction and a tail direction and a second angle including a first oblique direction and a second oblique direction with respect to the object of the examination; and a display control section configured to movie display the plurality of three-dimensional image data in which the view angle has been moved, on the monitor screen, under the condition of fixing the phase, and to determine, after one of the displayed plurality of three-dimensional image data is selected, an optimal view angle.

8. The image display apparatus according to claim 7, wherein the display control section displays the three dimensional image data on the monitor screen simultaneously as a synopsis, synchronizing the temporal elements.

9. An image display apparatus, comprising:

an image data preparing section configured to prepare a plurality of three-dimensional image data including temporal elements on an object of examination showing a periodic movement;

a color information defining section configured to automatically define a plurality of pieces of color information, each piece of color information corresponding to a quantity of contracting movement of the object of examination, and each piece of color information includes a plurality of viewing angles, each viewing angle comprising a combination of a first angle expressed in terms of a head direction and a tail direction and a second angle including a first oblique direction and a second oblique direction with respect to the object of the examination;

a monitor having a monitor screen; and a display control section configured to display an image on the monitor screen, and to add the color information to the plurality of three-dimensional image data based on predefined thresholds.

10. An image display apparatus, comprising:

an image data preparing section configured to prepare (1) a first moving image at an arbitrarily selected view angle including temporal elements from four-dimensional image data including temporal elements on an object of examination showing a periodic contracting movement for at least three phases in the contracting movement of the object of examination, and (2) a second moving image showing a plurality of view angles shifted from the arbitrarily selected view angle relative to the object of examination under the condition of fixing the contracting movement of the object of examination from the four-dimensional image data, each view angle comprising a combination of a first angle expressed in terms of a head direction and a tail direction and a second angle including a first oblique direction and a second oblique direction with respect to the object of the examination, each of the first and second moving images being a respective sequence of images;

a monitor having a monitor screen; and a display control section configured to alternatively movie display the first moving image and the second moving image in response to input by an operator, and to determine, based on the displayed moving images, an optimal view angle.

11. The image display apparatus according to claim 5, further comprising:
- medical equipment configured to image the object of examination from the view angles to pick up images thereof;
- a view angle determining section configured to determine the optimal view angle from the first three-dimensional image data and the second three-dimensional image data displayed on the monitor screen; and
- a transmission section configured to transmit the optimal view angle determined by the view angle determining section to the medical equipment,
- the medical equipment imaging the object of examination from the optimal view angle.

12. The image display apparatus according to claim 11, wherein
- the medical equipment is an X-ray apparatus; and
- the X-ray apparatus has a C arm for arranging an X-ray source and an X-ray detector opposite to each other and imaging the object of examination, moving the X-ray source and the X-ray detector to respective positions corresponding to the optimal view angle by driving the C arm to rotate according to the optimal view angle.

\* \* \* \* \*